United States Patent
Lim et al.

(10) Patent No.: US 7,932,365 B2
(45) Date of Patent: Apr. 26, 2011

(54) PREPARATION AND COMPOSITION OF INTER-ALPHA INHIBITOR PROTEINS FROM HUMAN PLASMA FOR THERAPEUTIC USE

(75) Inventors: Yow-Pin Lim, East Providence, RI (US); Djuro Josic, North Providence, RI (US); Douglas C. Hixson, Barrington, RI (US)

(73) Assignee: Pro Thera Biologics, LLC, East Providence, RI (US)

(*) Notice: Subject to any disclaimer, the term of this patent is extended or adjusted under 35 U.S.C. 154(b) by 1049 days.

(21) Appl. No.: 10/578,449

(22) PCT Filed: Nov. 5, 2004

(86) PCT No.: PCT/US2004/036848
§ 371 (c)(1),
(2), (4) Date: Apr. 4, 2007

(87) PCT Pub. No.: WO2005/046587
PCT Pub. Date: May 26, 2005

(65) Prior Publication Data
US 2007/0297982 A1    Dec. 27, 2007

Related U.S. Application Data

(60) Provisional application No. 60/518,366, filed on Nov. 8, 2003, provisional application No. 60/617,166, filed on Oct. 8, 2004.

(51) Int. Cl.
*A23J 1/00* (2006.01)
*C07K 14/435* (2006.01)
*C12Q 1/00* (2006.01)

(52) U.S. Cl. ............ 530/412; 435/4; 530/350

(58) Field of Classification Search .......... 530/384, 530/380, 412, 413, 414, 416, 417, 422, 829, 530/830; 424/529, 530
See application file for complete search history.

(56) References Cited

U.S. PATENT DOCUMENTS
5,777,081 A * 7/1998 Michalski et al. ........... 530/380
2003/0190732 A1 10/2003 Josic FOREIGN PATENT DOCUMENTS
WO    WO 0163280 A2 *  8/2001
WO    WO-02/30983      4/2002

OTHER PUBLICATIONS

J.-P. Salier et al. Biochem. J. (1996) 315, pp. 1-9.*
L. Odum. Biol. Chem. Hoppe-Seyler (1990) 371, pp. 1153-1158.*
Hoffer et al. Improved virus safety and purity of a chromatographically produced factor IX concentrate by nanofiltration. Journal of Chromatography B, 1995, vol. 669, pp. 187-196, especially pp. 187-190 and Figures 1-5.
Lim et al. Correlation between Mortality and the Levels of Inter-Alpha Inhibitors in Plasma of Patients with Severe Sepsis. The Journal of Infectious Diseases, Sep. 15, 2003, vol. 188, pp. 919-926, especially pp. 919, 920 and 925.
Yang et al. Administration of human inter-alpha-inhibitors maintains hemodynamic stability and improves survival during sepsis. Crit. Care. Med., 2002, vol. 30, No. 3, pp. 617-622, especially pp. 617-621.
Wu et al. Delayed administration of human inter-alpha inhibitor proteins reduces mortality in sepsis. Crit. Care. Med., 2004, vol. 32, No. 8 pp. 1747-1752, especially pp. 1747-1751 and Figures 1-5.
Lim et al. Affinity purification and enzymatic cleavage of inter-alpha inhibitor proteins using antibody and elastase immobilized on CIM monolithic disks. Journal of Chromatography A, 2005, vol. 1065, pp. 39-43.
EPO Form 1507.4, EP, Feb. 3, 2010, Supplementary European Search Report for 04810367.
Mizon, C. et al., "Human pre-[alpha]-inhibitor: Isolation from a by-product of industrial scale plasma fractionation and structural analysis of its H3 heavy chain", Journal of Chromatography B: Biomedical Applications 19970509 NL, vol. 692, No. 2, May 9, 1997.
Michalski, Catherine et al: "Preparation and properties of a therapeutic inter-alpha trypsin inhibitor concentrate from human plasma", Vox Sanguinis, vol. 67, No. 4, 1994, pp. 329-336.
Carrette, O. et al., "Purification and characterization of pig inter-alpha-inhibitor and its constitutive heavy chains", CA, STN, ZENT. Biol. chem., Universitaetsklin, Frankfurt, Germany, vol. 1338, No. 1, Mar. 7, 1997, pp. 21-30.
Salier, J.P. et al., ; "Purification of the human serum inter-alpha-trypsin inhibitor by zinc chelate and hydrophobic interaction chromatographies", Analytical Biochemistry, Academic Press, Inc. New York, vol. 109, No. 2, Dec. 1, 1980, pp. 273-283.
Salier, J.P., et al.,; "Inter-alpha-trypsin-inhibitor (ITI): Use of immunoadsorbents for preparation of anti-ITI antiserum, ITI-free human serum and purified ITI", Journal of Immunological Methods, Elsevier Science Publishers B.V., Amsterdam, NL, vol. 47, No. 2, Dec. 15, 1981, pp. 239-248.

* cited by examiner

*Primary Examiner* — Andrew D Kosar
(74) *Attorney, Agent, or Firm* — Edwards Angell Palmer & Dodge LLP; Peter C. Lauro, Esq.; Elbert Chiang

(57) ABSTRACT

The invention relates to Inter-alpha inhibitor proteins (IαIp). The invention further relates to processes for purification of IαIp compositions and their use for treatment of human diseases such as sepsis and septic shock, rheumatoid arthritis, cancer and infectious diseases.

25 Claims, 10 Drawing Sheets

Figure 1
A  B
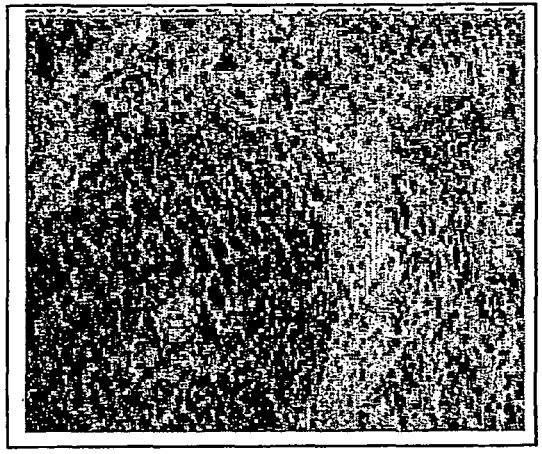
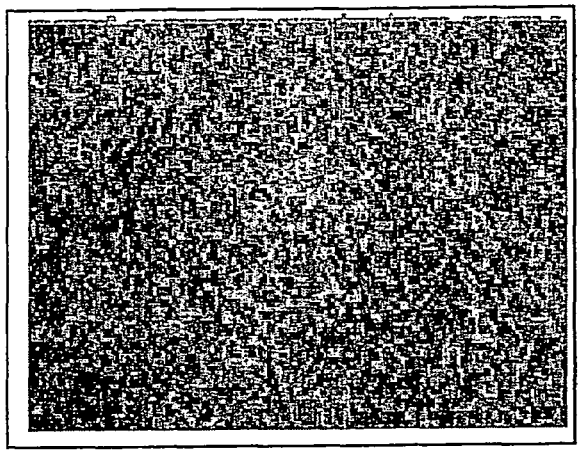

Figure 2

1 mkpprpvrtc skvlvllsll aihqtttaek ngidiysltv dsrvssrfah tvvtsrvvnr
61 antvqeatfq melpkkafit nfsmnidgmt ypgiikekae aqaqysaava kgksaglvka
121 tgrmmeqfqv svsvapnaki tfelvyeell krrlgvyell lkvrpqqlvk hlqmdihife
181 pqgisflete stfmtnqlvd alttwqnktk ahirfkptls qqqkspeqqe tvldgnliir
241 ydvdraisgg siqiengyfv hyfapegltt mpknvvfvid ksgsmsgrki qqtrealiki
301 lddlsprdqf nlivfsteat qwrpslvpas aenvnkarsf aagiqalggt nindamlmav
361 qlldssnqee rlpegsvsli illtdgdptv getnprsiqn nvreavsgry slfclgfgfd
421 vsyaflekla ldngglarri hedsdsalql qdfyqevanp lltavtfeyp snaveevtqn
481 nfrllfkgse mvvagklqdr gpdvltatvs gklptqnitf qtessvaeqe aefqspkyif
541 hnfmerlway ltiqqlleqt vsasdadqqa lmqalnlsl aysfvtplts mvvtkpddqe
601 qsqvaekpme gesrmrnvhs gstfffkyylq gakipkpeas fsprrgwnrq agaagsrmnf
661 rpgvlssrql glpgppdvpd haayhpfrrl ailpasappa tsnpdpavsr vmnmkieett
721 mttqtpapiq apsailplpg qsverlcvdp rhrqgpvnll sdpeqgvevt gqyerekagf
781 swievtfknp lvwvhaspeh vvvtrnrrss aykwketlfs vmpglkmtmd ktglllsdp
841 dkvtigllfw dgrgeglrll lrdtdrfssh vggtlgqfyq evlwgspaas ddgrrtlrvq
901 gndhsatrer rldyqegppg veiscwsvel

Figure 3
A
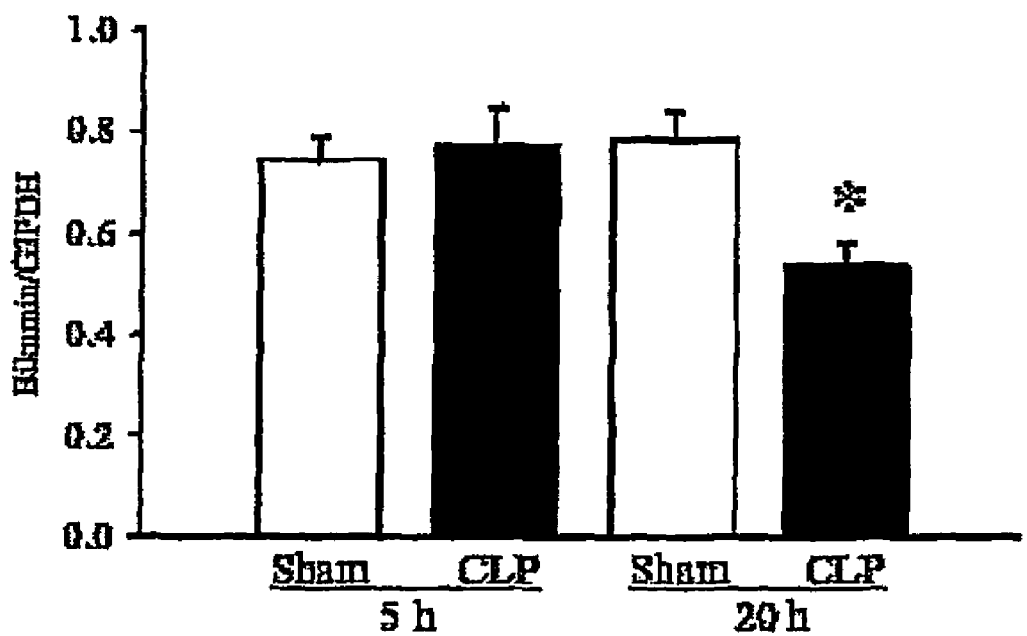
B

*p value=0.0293

SEQUENCE LISTING

```
<160> NUMBER OF SEQ ID NOS: 1

<210> SEQ ID NO 1
<211> LENGTH: 930
<212> TYPE: PRT
<213> ORGANISM: Homo sapiens

<400> SEQUENCE: 1

Met Lys Pro Pro Arg Pro Val Arg Thr Cys Ser Lys Val Leu Val Leu
1               5                   10                  15

Leu Ser Leu Leu Ala Ile His Gln Thr Thr Thr Ala Glu Lys Asn Gly
            20                  25                  30

Ile Asp Ile Tyr Ser Leu Thr Val Asp Ser Arg Val Ser Ser Arg Phe
        35                  40                  45

Ala His Thr Val Val Thr Ser Arg Val Val Asn Arg Ala Asn Thr Val
    50                  55                  60

Gln Glu Ala Thr Phe Gln Met Glu Leu Pro Lys Lys Ala Phe Ile Thr
65                  70                  75                  80

Asn Phe Ser Met Asn Ile Asp Gly Met Thr Tyr Pro Gly Ile Ile Lys
                85                  90                  95

Glu Lys Ala Glu Ala Gln Ala Gln Tyr Ser Ala Ala Val Ala Lys Gly
            100                 105                 110

Lys Ser Ala Gly Leu Val Lys Ala Thr Gly Arg Asn Met Glu Gln Phe
        115                 120                 125

Gln Val Ser Val Ser Val Ala Pro Asn Ala Lys Ile Thr Phe Glu Leu
    130                 135                 140

Val Tyr Glu Glu Leu Leu Lys Arg Arg Leu Gly Val Tyr Glu Leu Leu
145                 150                 155                 160

Leu Lys Val Arg Pro Gln Gln Leu Val Lys His Leu Gln Met Asp Ile
                165                 170                 175

His Ile Phe Glu Pro Gln Gly Ile Ser Phe Leu Glu Thr Glu Ser Thr
            180                 185                 190

Phe Met Thr Asn Gln Leu Val Asp Ala Leu Thr Thr Trp Gln Asn Lys
        195                 200                 205

Thr Lys Ala His Ile Arg Phe Lys Pro Thr Leu Ser Gln Gln Gln Lys
    210                 215                 220

Ser Pro Glu Gln Gln Glu Thr Val Leu Asp Gly Asn Leu Ile Ile Arg
225                 230                 235                 240

Tyr Asp Val Asp Arg Ala Ile Ser Gly Gly Ser Ile Gln Ile Glu Asn
                245                 250                 255

Gly Tyr Phe Val His Tyr Phe Ala Pro Glu Gly Leu Thr Thr Met Pro
            260                 265                 270

Lys Asn Val Val Phe Val Ile Asp Lys Ser Gly Ser Met Ser Gly Arg
```

-continued

```
                275                 280                 285
Lys Ile Gln Gln Thr Arg Glu Ala Leu Ile Lys Ile Leu Asp Asp Leu
290                 295                 300
Ser Pro Arg Asp Gln Phe Asn Leu Ile Val Phe Ser Thr Glu Ala Thr
305                 310                 315                 320
Gln Trp Arg Pro Ser Leu Val Pro Ala Ser Ala Glu Asn Val Asn Lys
                325                 330                 335
Ala Arg Ser Phe Ala Ala Gly Ile Gln Ala Leu Gly Gly Thr Asn Ile
                340                 345                 350
Asn Asp Ala Met Leu Met Ala Val Gln Leu Leu Asp Ser Ser Asn Gln
                355                 360                 365
Glu Glu Arg Leu Pro Glu Gly Ser Val Ser Leu Ile Ile Leu Leu Thr
370                 375                 380
Asp Gly Asp Pro Thr Val Gly Glu Thr Asn Pro Arg Ser Ile Gln Asn
385                 390                 395                 400
Asn Val Arg Glu Ala Val Ser Gly Arg Tyr Ser Leu Phe Cys Leu Gly
                405                 410                 415
Phe Gly Phe Asp Val Ser Tyr Ala Phe Leu Glu Lys Leu Ala Leu Asp
                420                 425                 430
Asn Gly Gly Leu Ala Arg Arg Ile His Glu Asp Ser Asp Ser Ala Leu
                435                 440                 445
Gln Leu Gln Asp Phe Tyr Gln Glu Val Ala Asn Pro Leu Leu Thr Ala
450                 455                 460
Val Thr Phe Glu Tyr Pro Ser Asn Ala Val Glu Glu Val Thr Gln Asn
465                 470                 475                 480
Asn Phe Arg Leu Leu Phe Lys Gly Ser Glu Met Val Val Ala Gly Lys
                485                 490                 495
Leu Gln Asp Arg Gly Pro Asp Val Leu Thr Ala Thr Val Ser Gly Lys
                500                 505                 510
Leu Pro Thr Gln Asn Ile Thr Phe Gln Thr Glu Ser Ser Val Ala Glu
                515                 520                 525
Gln Glu Ala Glu Phe Gln Ser Pro Lys Tyr Ile Phe His Asn Phe Met
530                 535                 540
Glu Arg Leu Trp Ala Tyr Leu Thr Ile Gln Gln Leu Leu Glu Gln Thr
545                 550                 555                 560
Val Ser Ala Ser Asp Ala Asp Gln Gln Ala Leu Arg Asn Gln Ala Leu
                565                 570                 575
Asn Leu Ser Leu Ala Tyr Ser Phe Val Thr Pro Leu Thr Ser Met Val
                580                 585                 590
Val Thr Lys Pro Asp Asp Gln Glu Gln Ser Gln Val Ala Glu Lys Pro
                595                 600                 605
Met Glu Gly Glu Ser Arg Asn Arg Asn Val His Ser Gly Ser Thr Phe
610                 615                 620
Phe Lys Tyr Tyr Leu Gln Gly Ala Lys Ile Pro Lys Pro Glu Ala Ser
625                 630                 635                 640
Phe Ser Pro Arg Arg Gly Trp Asn Arg Gln Ala Gly Ala Ala Gly Ser
                645                 650                 655
Arg Met Asn Phe Arg Pro Gly Val Leu Ser Ser Arg Gln Leu Gly Leu
                660                 665                 670
Pro Gly Pro Pro Asp Val Pro Asp His Ala Ala Tyr His Pro Phe Arg
                675                 680                 685
Arg Leu Ala Ile Leu Pro Ala Ser Ala Pro Pro Ala Thr Ser Asn Pro
690                 695                 700
```

-continued

| | | | | | | | | | | | | | | | |
|---|---|---|---|---|---|---|---|---|---|---|---|---|---|---|---|
| Asp | Pro | Ala | Tyr | Ser | Arg | Val | Met | Asn | Met | Lys | Ile | Glu | Glu | Thr | Thr |
| 705 | | | | | 710 | | | | | 715 | | | | | 720 |
| Met | Thr | Thr | Gln | Thr | Pro | Ala | Pro | Ile | Gln | Ala | Pro | Ser | Ala | Ile | Leu |
| | | | | 725 | | | | | 730 | | | | | 735 | |
| Pro | Leu | Pro | Gly | Gln | Ser | Val | Glu | Arg | Leu | Cys | Val | Asp | Pro | Arg | His |
| | | | 740 | | | | | 745 | | | | | 750 | | |
| Arg | Gln | Gly | Pro | Val | Asn | Leu | Leu | Ser | Asp | Pro | Glu | Gln | Gly | Val | Glu |
| | | 755 | | | | | 760 | | | | | 765 | | | |
| Val | Thr | Gly | Gln | Tyr | Glu | Arg | Glu | Lys | Ala | Gly | Phe | Ser | Trp | Ile | Glu |
| | 770 | | | | | 775 | | | | | 780 | | | | |
| Val | Thr | Phe | Lys | Asn | Pro | Leu | Val | Trp | Val | His | Ala | Ser | Pro | Glu | His |
| 785 | | | | | 790 | | | | | 795 | | | | | 800 |
| Val | Val | Val | Thr | Arg | Asn | Arg | Arg | Ser | Ser | Ala | Tyr | Lys | Trp | Lys | Glu |
| | | | | 805 | | | | | 810 | | | | | 815 | |
| Thr | Leu | Phe | Ser | Val | Met | Pro | Gly | Leu | Lys | Met | Thr | Met | Asp | Lys | Thr |
| | | | 820 | | | | | 825 | | | | | 830 | | |
| Gly | Leu | Leu | Leu | Leu | Ser | Asp | Pro | Asp | Lys | Val | Thr | Ile | Gly | Leu | Leu |
| | | 835 | | | | | 840 | | | | | 845 | | | |
| Phe | Trp | Asp | Gly | Arg | Gly | Glu | Gly | Leu | Arg | Leu | Leu | Leu | Arg | Asp | Thr |
| | 850 | | | | | 855 | | | | | 860 | | | | |
| Asp | Arg | Phe | Ser | Ser | His | Val | Gly | Gly | Thr | Leu | Gly | Gln | Phe | Tyr | Gln |
| 865 | | | | | 870 | | | | | 875 | | | | | 880 |
| Glu | Val | Leu | Trp | Gly | Ser | Pro | Ala | Ala | Ser | Asp | Asp | Gly | Arg | Arg | Thr |
| | | | | 885 | | | | | 890 | | | | | 895 | |
| Leu | Arg | Val | Gln | Gly | Asn | Asp | His | Ser | Ala | Thr | Arg | Glu | Arg | Arg | Leu |
| | | | 900 | | | | | 905 | | | | | 910 | | |
| Asp | Tyr | Gln | Glu | Gly | Pro | Pro | Gly | Val | Glu | Ile | Ser | Cys | Trp | Ser | Val |
| | | 915 | | | | | 920 | | | | | 925 | | | |
| Glu | Leu | | | | | | | | | | | | | | |
| | 930 | | | | | | | | | | | | | | |

PREPARATION AND COMPOSITION OF INTER-ALPHA INHIBITOR PROTEINS FROM HUMAN PLASMA FOR THERAPEUTIC USE

This application is a U.S. national phase application, pursuant to 35 U.S.C. §371, of PCT international application Ser. No. PCT/US04/036848 filed Nov. 5, 2004, designating the United States and published in English on May 26, 2005 as publication WO 2005/046587 A2, which claims priority to U.S. provisional applications Ser. No. 60/518,366, filed Nov. 8, 2003, and Ser. No. 60/617,166, filed Oct. 8, 2004. The entire contents of the aforementioned patent applications are incorporated herein by this reference.

RELATED APPLICATION

This application contains subject matter that is related to that disclosed in provisional patent application Ser. No. 60/518,366 filed Nov. 8, 2003, entitled, "Preparation and Composition of Inter-alpha Inhibitor Proteins from Human Plasma for Therapeutic Use," the disclosure of which application is incorporated herein in its entirety by this reference.

GOVERNMENT SUPPORT

A portion of this invention may have been supported by National Institutes of Health grants RO1 GM053008, R01 GM057468, and R43 GM065667.

BACKGROUND OF THE INVENTION

The inter-alpha inhibitor protein (IαIp) family is a group of plasma-associated serine protease inhibitors. Members of this family are composed of heavy and light polypeptide subunits that are covalently linked by a glycosaminoglycan. The light chain, also called bikunin, is responsible for the serine protease inhibitory activity of the molecules. The name "bikunin" reflects the presence of 2 protease-inhibiting domains of the Kunitz type. In normal plasma, bikunin is found mostly in a complex form as inter-alpha inhibitor (IαI), which has a molecular weight of 225 kDa, and pre-alpha inhibitor (PαI), which has molecular weight of 120 kDa. In IαI, bikunin is linked to 2 heavy polypeptide chains, H1 and H2, whereas, in PαI, only a single heavy chain (H3) is linked to bikunin. In these complexed forms, bikunin remains inactive until its release by partial proteolytic degradation, a mechanism that serves as a means to regulate activity. After cleavage from the complex, the activated bikunin is cleared rapidly from plasma by glomerular filtration, a process that is facilitated by its low molecular weight and by receptor-mediated uptake. U.S. Pat. Nos. 6,489,128 and 6,660,482 are related to the use of diagnosing cancer and sepsis, respectively. Methods of inhibiting metastases and of treating sepsis are also disclosed, however, the compositions were not substantially pure and had stability, i.e., short half-lives, problems.

Despite the introduction of antibiotics over fifty years ago, which indeed saw a decline of sepsis-induced mortality from 55% to 35%, medicine has not benefited from a significant reduction in mortality of subjects with sepsis. In fact, sepsis continues to be one of the leading causes of death in intensive care units and a large number of septic subjects die of ensuing septic shock and multiple organ failure. Sepsis is a systemic response to infection, e.g., a bacterial infection. It is commonly caused by endotoxins from Gram negative bacteria or exotoxins from Gram positive bacteria (which can trigger endotoxin-like responses). The systemic response can lead to septic shock, which is characterized by a precipitous drop in blood pressure, cardiovascular collapse, and/or multiple organ failure. The mortality rate among subjects diagnosed with septic shock can be as high as 35-45%. Rapidly and reliably treating sepsis has been difficult using conventional medications.

Sepsis and septic shock are associated with activation of innate immunity and coagulation systems. Sepsis and septic shock are characterized clinically by systemic inflammation, coagulopathy, hypotension and multiple organ dysfunction (J.-L. Vincent et al., Annuals of Medicine 34 (2002) 606-613). During severe sepsis, a network of specific proteases activates clotting, fibrinolytic and complement factors. These proteases can also trigger tissue and organ damage and enhance non-specific proteolysis of clotting and complement factors in plasma (J. Wite et al., Intensive Care Medicine 8 (1982) 215-222; S. J. Weiss, New England Journal of Medicine 320 (1989) 365-376).

BRIEF SUMMARY OF THE INVENTION

The present invention relates to a process for the purification of inter-alpha inhibitor proteins (IαIp) from human plasma and their use for treatment of human diseases such as sepsis, acute inflammatory diseases, severe shock, septic shock, rheumatoid arthritis, cancer, cancer metastasis, infectious diseases, and preterm labor; or reducing the risk of mortality associated with sepsis, acute inflammatory diseases, severe shock, septic shock, rheumatoid arthritis, cancer, cancer metastasis, infectious diseases, and preterm labor.

According to one aspect, a process for producing a blood plasma-derived IαIp composition, wherein IαI and PαI are present in the mixture in a physiological proportion comprises isolating from blood plasma a plasma fraction containing IαI and PαI, wherein the IαI and PαI are present in a physiological proportion; and purifying the plasma fraction to obtain an IαIp composition with a purity of IαIp ranging from about 85% to about 100% pure.

According to another aspect a composition of IαIp comprises a mixture of inter-alpha inhibitor protein (IαI) and pre-alpha protein (PαI), wherein the IαI and the PαI are present in said mixture in a physiological proportion ranging from about 85% to about 100% pure.

In a related aspect, a composition of IαIp comprises a mixture of inter-alpha inhibitor protein (IαI) and pre-alpha protein (PαI), wherein the IαI and the PαI are present in said mixture in a physiological proportion and having a high trypsin inhibitory specific activity.

In another related aspect, a composition of IαIp comprises IαI and PαI having a half-life of greater than one hour.

In yet another related aspect, a composition of IαIp comprises IαI and PαI wherein the IαI and PαI are composed of a light chain of inter-alpha inhibitor protein associated with at least one of three heavy chains H1, H2 and H3.

In another related aspect, a composition of IαIp comprises a mixture of inter-alpha inhibitor protein (IαI) and pre-alpha protein (PαI), wherein the IαI and the PαI are present in the mixture in a physiological proportion comprising a light chain of inter-alpha inhibitor protein associated with at least one of four heavy chains-H1, H2, H3 and H4.

In still another related aspect, a composition of IαIp is made according to the process, which comprises isolating from blood plasma a plasma fraction containing IαI and PαI, wherein the IαI and PαI are present in a physiological proportion; and purifying the plasma fraction to obtain an IαIp composition with a purity of IαIp ranging from about 85% to about 100% pure.

In another aspect, a pharmaceutical composition according to the invention comprises a therapeutically effective composition of IαIp as described herein and a pharmaceutically acceptable carrier.

Another aspect relates to a method of treating an inflammation related disorder, cancer, or an infectious disease in a subject, which comprises administering a therapeutically effective amount of IαIp produced by any of the processes described infra.

In another related aspect, a method of treating a subject comprises determining the pre-treatment level of one or more of IαI, PαI, IαIp, H3, H4, H1, H2, and LC; and administering a therapeutically effective amount of IαIp to the subject.

In a related aspect, a method for predicting a response to an IαIp therapy is described. The method comprises assaying a sample obtained from a subject to detect the level of one or more of IαI, PαI, IαIp, H3, H4, H1, H2, and LC; wherein the detected levels identifies a subject that may respond favorable to IαIp therapy.

In another related aspect, a method of monitoring the progress of a subject being treated with an IαIp therapy is described and comprises determining the pre-treatment level of one or more of IαI, PαI, IαIp, H3, H4, H1, H2, and LC; administering a therapeutically effective amount of IαIp to the subject; and determining the level of one or more of the levels in the subject after an initial period of treatment with the IαIp, wherein an increase of the level in the subject following treatment with IαIp indicates that the subject is likely to have a favorable clinical response to treatment with IαIp.

In another aspect, a kit for IαIp therapy is described and comprises one or more of IαI, PαI, IαIp, H3, H4, H1, H2, and LC; and instructions for therapeutic use.

In a related aspect, a composition is described, which comprises a container including IαIp and a label or package insert with instructions for administering the IαIp to a subject.

In a further related aspect, a kit is described, which comprises a composition as described above as well as instructions for therapeutic use.

Other embodiments of the invention are disclosed infra.

BRIEF DESCRIPTION OF THE DRAWINGS

FIG. 1 depicts histopathology of the spleen. Penicillary artery surrounded by preserved white pulp with extensive loss of red pulp cellular elements in the control animal (A) versus in the IαIp-treated animal (B) with normal surrounding white pulp and slightly hypercellular red pulp (H&E stain, magnification 20×).

FIG. 2 depicts the amino acid sequence of H4 (SEQ ID NO: 1).

FIG. 3 depicts the alterations in bikunin mRNA expression in the liver at 5 and 20 h after cecal ligation and puncture (CLP) or sham operation (Sham). Data are expressed as means ±SE (n=8/group) and compared by one-way analysis of variance (ANOVA) and Tukey's test: * P<0.05 versus shams. FIG. 3a shows the mRNA amplified and separated by size on a gel, and FIG. 3b graphically depicts the results with the bikunin levels being normalized to the G3PDH expression.

DETAILED DESCRIPTION OF THE INVENTION

Figure 4:
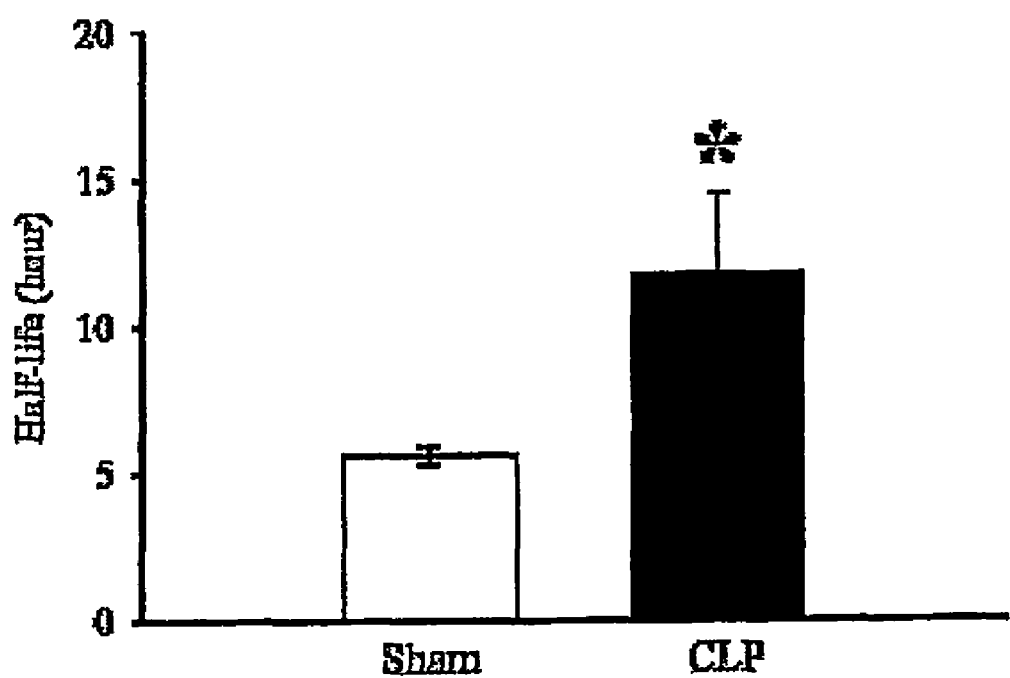
FIG. 4 depicts the alterations in the $t_{1/2}$ of 125I-IαI at 5 and 20 h after cecal ligation and puncture (CLP) or sham operation (Sham). Data are expressed as means ±SE (n=5/group) and compared by one-way analysis of variance (ANOVA) and Tukey's test.

Disclosed herein is a new process for purifying IαIp from plasma. Further disclosed herein is a therapeutic composition of purified IαIp for administration to a subject to treat acute inflammatory disease, sepsis, severe shock, septic shock, rheumatoid arthritis, cancer, cancer metastasis, infectious disease, and preterm labor.

Prior known purifications contained contamination by factor X (FX), which is detected as an 80 kDa band by Western blot analysis. The FX was also detected in a clotting assay. The removal of FX is important because FX is considered thrombogenic and can be harmful if administered to humans. The methods described herein solve the FX contamination problems of previous IαIp compositions.

Inter-alpha inhibitor proteins (IαIp) are a family of structurally related serine protease inhibitors found at relatively high concentrations (400-800 mg/L) in human plasma. IαIp is a large, multi-component complex that functions as a trypsin-type protease inhibitor. Unlike other inhibitor molecules, this family of inhibitors consists of a combination of polypeptide chains (light and heavy chains) covalently linked uniquely by a chondroitin sulfate chain. The heavy chains of Inter-alpha proteins (H1, H2 and H3) are also called Hyaluronic acid (HA) binding proteins. The major forms found in human plasma are inter-alpha-inhibitor (IαI), which consists of two heavy chains (H1 & H2) and a single light chain (L), and pre-alpha-inhibitor (PαI), which consists of one heavy (H3) and one light chain (L). The light chain (also termed bikunin (bi-kunitz inhibitor, having two Kunitz domains) is known to broadly inhibit plasma serine proteases. The complex has been shown to be important in the inhibition of an array of proteases, including neutrophil elastase, plasmin, trypsin, chymotrypsin, cathepsin G, and acrosin.

IαI and PαI have also been found to be complexed with H4, another heavy chain of IαIp proteins. Certain embodiments of IαIp compositions according to the invention contain H4 in complex with PαI, IαI, or both PαI and IαI.

Without wishing to be bound by any scientific theories, we speculate that heavy chains of IαIp, after being released from the complex, bind HA preventing HA from binding its receptor, CD44. In the absence of heavy chains of IαIp, HA will bind to CD44 and trigger the secretion of pro-inflammatory factors, for example, TNF-alpha, and cause inflammation.

Meanwhile, the light chains of IαIp, once released from the complex exhibit anti-protease activity.

"IαIp composition" refers to a preparation of IαIp proteins, including IαI and PαI in physiological proportions. Physiological proportions, as used herein is intended to include proportions found in a person or animal that is not suffering from an infection or condition, and/or the ratio of IαI to PαI that appears naturally in human plasma. Physiological proportions are usually from between about 60% to about 80% IαI and between about 40% to about 20% PαI. Physiological proportions may vary from these ranges due to normal variations in genetic makeup of subjects.

As used herein, "mixture of inter-alpha inhibitor protein (IαI) and pre-alpha protein (PαI)" refers to a composition containing both the IαI and PαI complexes. The mixture may also contain buffers, salts, or other components that are used to isolate the IαIp complex. In certain aspects, the IαI and the PαI are present in the mixture in a physiological proportion.

IαI and PαI present in the plasma fraction have an apparent molecular weight of between about 60,000 to about 280,000 kDa. Molecular weight may be determined by sodium dodecyl sulfate polyacrylamide gel electrophoresis.

"Half-life," as used herein, refers to half of the amount of time that the administered IαIp is active upon administration. IαIp compositions according to the invention have a half-life of, for example, greater than about 1, 1.5, 2, 2.5, 3, 3.5, 4, 4.5, 5, 7.5, or 10 hours. In a preferred embodiment, the IαIp composition has a half-life of greater than about 5 hours. In a particularly preferred embodiment, the IαIp composition has a half-life of greater than about 10 hours. Longer half-lives are preferred, for example, because fewer doses are required to be administered to a subject over time.

The IαIp compositions of the invention may have a high trypsin inhibitory specific activity. The trypsin inhibitory specific activity of the IαIp compositions according to the invention may range from between about 1000 to about 2000 IU/mg. Preferably the trypsin inhibitory specific activity is above 1200 IU/mg and even more preferably above 1500 IU/mg. The trypsin inhibitory specific activity may be measured, for example, by the trypsin inhibitory assay using L-BAPA as a substrate. See, H U Bergmeyer, ed: vol 5, $3^{rd}$ ed. 119 (1984) Verlag Chemie, Weinheim: Chromogenic substrate for the assay of trypsin: R. Geiger, H. Fritz, Methods of Enzymatic Analysis.

A composition of IαIp may be a mixture of inter-alpha inhibitor protein (IαI) and pre-alpha protein (PαI), wherein the IαI and the PαI are present in said mixture in a physiological proportion comprising a light chain of inter-alpha inhibitor protein associated with at least one of three heavy chains H1, H2 and H3. A composition according to the invention may also have a light chain of inter-alpha inhibitor protein associated with at least one of four heavy chains H1, H2, H3 and H4. Examples of each protein in the IαIp complex are as follows: Bikunin GenBank accession number: AAB84031, P02760; H1 GenBank accession number: P19827, NP_002206; H2 GenBank accession number: NP_002207, P19823; H3 GenBank accession number: NP_002208; H4 GenBank accession number: Q14624, NP_002209, which are each incorporated herein by reference in their entirety.

As used herein "blood plasma-derived" refers to being originally isolated or purified from blood plasma. That is, the natural environment of the composition is blood plasma.

As used herein, "a plasma fraction" is a fraction from an isolation or purification step, for example, chromatography, that was originally derived from blood plasma. Plasma fractions according to the invention may be for example, a side fraction obtained from the purification of clotting factor IX, a side fraction from the purification of a prothrombin complex concentrate, a cryosupernatant resulting from cryoprecipitation (described in Hoffer et al., Journal of Chromatography B 669 (1995) 187-196) of blood plasma, or cryo-poor plasma cryo-poor plasma is used interchangeably with cryosupernatant herein. The cryo-poor plasma is the supernatant obtained from cryoprecipitation.

An example of a side fraction according to the invention is one obtained from the purification of clotting factor IX. A mixture of IαI/PαI has been shown to be present in sidefractions generated during the purification of factor IX (FIX). The method of obtaining the side fraction obtained from the purification of clotting factor IX is described in Hoffer et al., Journal of Chromatography B 669 (1995) 187-196, which is hereby incorporated by reference in its entirety. Other examples of side fractions include a side fraction from FIX purification or a side fraction from the purification of a prothrombin complex concentrate, as is described in D. Josic et al., Thrombosis Research 100 (2000) 433-441, which is hereby incorporated by reference in its entirety; and a side fraction isolated as a cryosupernatant resulting from cryoprecipitation of blood plasma. (For example, suitable cryoprecipitation methods are described in Hoffer et al., Journal of Chromatography B 669 (1995) 187-196.) Other plasma fractions that may be useful to purify IαIp complexes from blood include strong anion-exchange fractions and monolith chromatographic fractions, which are described below in the examples.

Plasma fractions, according to the invention, may be from human, primate, bovine, porcine, feline, or canine sources.

As used herein, the term "obtaining" includes purchasing, synthesizing, isolating or otherwise acquiring one or more of the substances used in practicing the invention.

Thus, "obtaining blood," as used herein, includes acquiring blood, for example, from human, primate, bovine, porcine, feline, or canine sources. The blood may be acquired and/or purchased from, for example, blood banks, hospitals, hospices, private companies, research foundations, or any other source of blood.

"Obtaining blood plasma," as used herein, includes acquiring blood plasma, for example, from human, primate, bovine, porcine, feline, or canine sources. The blood plasma may be acquired and/or purchased from, for example, blood banks, hospitals, hospices, private companies, research foundations, or any other source of blood. Alternately, blood plasma may also be isolated from blood once blood is obtained. Suitable methods of isolating blood plasma include gravity and centrifugation.

As used herein, "obtaining a side fraction obtained from the purification of clotting factor IX," includes acquiring and/or purchasing side fractions obtained from the purification of clotting factor IX from for example, a company or hospital that routinely purifies factor IX.

As used herein, "obtaining a side fraction from the purification of a prothrombin complex concentrate," includes acquiring and/or purchasing the side fractions, for example, from a company, research organization or hospital that purifies prothrombin complex.

As used herein, "obtaining a cryosupernatant resulting from cryoprecipitation of blood plasma," includes acquiring and/or purchased a cryosupernatant, for example, from a hospital, research organization, or company that cryopercipitates blood plasma in a manner suitable for use in the invention.

"Solid support" refers to a solid material which can be derivatized with, or otherwise attached to, a capture reagent. Exemplary solid supports include probes, microtiter plates and chromatographic resins.

"Adsorption" refers to detectable non-covalent binding of an analyte to an adsorbent or capture reagent. An adsorbent surface refers to a surface to which is bound an adsorbent (also called a "capture reagent" or an "affinity reagent"). An adsorbent is any material capable of binding an analyte (e.g., a target polypeptide or nucleic acid).

A chromatographic adsorbent refers to a material typically used in chromatography. Chromatographic adsorbents include, for example, ion exchange materials, metal chelators (e.g., nitriloacetic acid or iminodiacetic acid), immobilized metal chelates, hydrophobic interaction adsorbents, hydrophilic interaction adsorbents, dyes, simple biomolecules (e.g., nucleotides, amino acids, simple sugars and fatty acids) and mixed mode adsorbents (e.g., hydrophobic attraction/electrostatic repulsion adsorbents).

A biospecific adsorbent refers to an adsorbent comprising a biomolecule, e.g., a nucleic acid molecule (e.g., an aptamer), a polypeptide, a polysaccharide, a lipid, a steroid or a conjugate of these (e.g., a glycoprotein, a lipoprotein, a glycolipid, a nucleic acid (e.g., DNA)-protein conjugate). In certain instances the biospecific adsorbent can be a macromolecular structure such as a multiprotein complex, a biological membrane or a virus. Examples of biospecific adsorbents are antibodies, receptor proteins and nucleic acids. Biospecific adsorbents typically have higher specificity for a target analyte than chromatographic adsorbents.

"Eluent" or "wash solution" refers to an agent, typically a solution, which is used to affect or modify adsorption of an analyte to an adsorbent surface and/or remove unbound materials from the surface. The elution characteristics of an eluant can depend, for example, on pH, ionic strength, hydrophobicity, degree of chaotropism, detergent strength and temperature.

"Analyte" refers to any component of a sample that is desired to be detected. The term can refer to a single component or a plurality of components in the sample.

The terms "polypeptide," "peptide," and "protein" are used interchangeably herein to refer to a polymer of amino acid residues. The terms apply to amino acid polymers in which one or more amino acid residues are analogs or mimetics of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" includes glycoproteins, as well as non-glycoproteins.

"Immunoassay" is an assay that uses an antibody to specifically bind an antigen (e.g., an IαIp complex). The immunoassay is characterized by the use of specific binding properties of a particular antibody to isolate, target, and/or quantify the antigen.

"Antibody" refers to a polypeptide ligand substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well-characterized fragments produced by digestion with various peptidases. This includes, e.g., Fab' and F(ab)'$_2$ fragments. Antibodies includes polyclonal and monoclonal antibodies, chimeric, single chain, and humanized antibodies, as well as Fab fragments, including the products of an Fab or other immunoglobulin expression library.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to the IαIp complex from a specific species such as rat, mouse, or human can be selected to obtain only those polyclonal antibodies that are specifically immunoreactive with IαIp complex and not with other proteins, except for polymorphic variants and alleles of the IαIp complex. This selection may be achieved by subtracting out antibodies that cross-react with the IαIp complex molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

"Functionally equivalent" as used herein refers to any protein capable of exhibiting a substantially similar in vivo or in vitro activity as the IαIp proteins described herein, e.g., effecting a decrease in sepsis.

IαIp product structure and purity may be confirmed by, for example, HPLC or other chromatographic method known to one of skill in the art.

As used herein, "IαIp complex" is intended to encompass all naturally occurring biologically active variants of the IαIp proteins, including proteins containing deletions, insertions, additions, and substitutions. A "natural variant" of an IαIp protein is defined as a peptide obtained from plasma having a sequence that is altered by one or more amino acids. The variant may have "conservative" changes, wherein a substituted amino acid has similar structural or chemical properties, e.g., replacement of leucine with isoleucine. In other embodiments, a variant may have "nonconservative" changes, e.g., replacement of a glycine with a tryptophan. Similar variations may also include amino acid deletions or insertions, or both. Guidance in determining which and how many amino acid residues may be substituted, inserted or deleted without abolishing biological or immunological activity may be found using computer programs well known in the art, for example, DNASTAR software.

A "deletion" is defined as a change in either amino acid or nucleotide sequence in which one or more amino acid or nucleotide residues, respectively, are absent.

An "insertion" or "addition" is that change in an amino acid or nucleotide sequence which has resulted in the addition of one or more amino acid or nucleotide residues, respectively, as compared to the naturally occurring IαIp complex.

A "substitution" results from the replacement of one or more amino acids or nucleotides by different amino acids or nucleotides, respectively.

The term "biologically active" refers to having structural, regulatory or biochemical functions of a naturally occurring IαIp complex. Likewise, "immunologically active" defines the capability of the natural, recombinant or synthetic IαIp complex, or any oligopeptide thereof, to induce a specific immune response in appropriate animals or cells and to bind with specific antibodies.

The term "derivative" as used herein refers to the chemical modification of a nucleic acid encoding IαIp complex or the encoded IαIp complex. Illustrative of such modifications would be replacement of hydrogen by an alkyl, acyl, or amino group. A nucleic acid derivative would encode a polypeptide which retains essential biological characteristics of natural IαIp complex.

"Purifying," as used herein, refers to steps or processes of removing unwanted or contaminating proteins or components from IαIp to produce a purified IαIp complex. For example, a plasma fraction containing IαI and PαI in physiological proportion may be run through a series of chromatography steps to purify the IαIp composition.

"Isolating," as used herein refers to producing a plasma fraction from blood plasma, which contains IαI and PαI in physiological proportions. For example, isolating a plasma fraction may be achieved in accordance with the invention by chromatographing blood plasma. Isolated refers to material removed from its original environment (e.g., the natural environment if it is naturally occurring), and thus is altered "by the hand of man" from its natural state. For example, an isolated polypeptide or protein could be a component of blood plasma, or could be contained within a cell and be considered "isolated" because that blood plasma or particular cell may not be the original environment of the polypeptide.

Chromatographing, as used herein, may include anion-exchange chromatography. Anion-exchange chromatography may be particle-based, for example, DEAE Sepharose, DEAE Sephadex A50, Toyopearl DEAE, TMAE Fractogel, DEAE Fractogel, or Q-Sepharose. Anion-exchange chromatography may also be by monolithic support, for example, CIM with immobilized anion-exchange ligands such as DEAE-CIM or Q-CIM. SEPHAROSE is a trade name of Pharmacia, Inc. of New Jersey for a high molecular weight substance for the separation by gel filtration of macromolecules. Anion exchange columns have two components, a matrix and a ligand. The matrix can be, for example, cellulose, dextrans, agarose or polystyrene. The ligand can be diethylaminoethyl (DEAE), polyethyleneimine (PEI) or a quaternary ammonium functional group. The strength of an anion exchange column refers to the state of ionization of the ligand. Strong anionic exchange columns, such as, those, having a quaternary ammonium ligand, bear a permanent positive charge over a wide pH range. In weak anion exchange columns, such as DEAE and PEI, the existence of the positive charge depends on the pH of the column. Strong anion exchange columns such as Q Sepharose FF, or metal-chelating Sepharose (e.g., Cu2+-chelating Sepharose) are preferred. Anion exchange columns are generally loaded with a low-salt buffer at a pH above the pI of a-glucosidase.

The IαIp compositions of the invention are preferably from between about 85% to about 100% pure. As used herein, the term "pure" refers to the IαIp composition that is removed from its natural environment, isolated or separated, and is at least between about 85% to about 100% free, preferably 90% free, and more preferably 95% free from other components with which it is naturally associated. In preferred embodiments, a substantially purified protein will constitute more than 85%, 87.5%, 90%, 92.5%, 95%, 99% or even more of the proteins in the composition.

A peptide, polypeptide or protein that is "purified to homogeneity," as applied to the present invention, means that the peptide, polypeptide or protein has a level of purity where the peptide, polypeptide or protein is substantially free from other proteins and biological components. Any suitable materials and methods can be used to perform the isolation step or steps of blood plasma to obtain purified IαIp.

Typically, preparation of IαIp involves isolation of the sample and collection of fractions determined to contain the proteins of interest. Methods of isolation include, for example, solid phase extraction, chromatography, for example anion-exchange chromatography, size exclusion chromatography, ion exchange chromatography, heparin chromatography, affinity chromatography, sequential extraction, gel electrophoresis and liquid chromatography. Preparation may also include purifying, which may include the steps of chromatography, for example, ion exchange chromatography, heparin chromatography, affinity chromatography, sequential extraction, gel electrophoresis and liquid chromatography.

In one embodiment of the invention, a sample can be purified twice by anion exchange chromatography. Anion exchange chromatography allows purification of the proteins in a sample roughly according to their charge characteristics. For example, a Q anion-exchange resin can be used (e.g., Q HyperD F, Biosepra), and a sample can be sequentially eluted with eluants having different pH's. Anion exchange chromatography allows separation of biomolecules in a sample that are more negatively charged from other types of biomolecules. Proteins that are eluted with an eluant having a high pH is likely to be weakly negatively charged, and a fraction that is eluted with an eluant having a low pH is likely to be strongly negatively charged. Thus, in addition to reducing complexity of a sample, anion exchange chromatography separates proteins according to their binding characteristics.

In yet another embodiment, a sample can be further purified by heparin chromatography. Heparin chromatography allows further purification of the IαIp complexes in a sample also on the basis of affinity interaction with heparin and charge characteristics. Heparin, a sulfated mucopolysaccharide, will bind IαIp complexes with positively charged moieties and a sample can be sequentially eluted with eluants having different pH's or salt concentrations. IαIp complexes eluted with an eluant having a low pH are more likely to be weakly positively charged. IαIp complexes eluted with an eluant having a high pH are more likely to be strongly positively charged. Thus, heparin chromatography also reduces the complexity of a sample and separates IαIp complexes according to their binding characteristics.

IαIp complexes may be may be captured with capture reagents immobilized to a support, such as any biochip, a multiwell microtiter plate, a resin, or nitrocellulose membranes that are subsequently probed for the presence of proteins. In particular, the IαIp complexes of this invention may be captured on Surface-Enhanced Laser Desorption/Ionization (SELDI) protein biochips. Capture can be on a chromatographic surface or a biospecific surface. Any of the SELDI protein biochips comprising reactive surfaces can be used to capture and detect the IαIp complexes of this invention. These biochips can be derivatized with the antibodies that specifically capture the IαIp complexes, or they can be derivatized with capture reagents, such as protein A or protein G that bind immunoglobulins. Then the IαIp complexes can be captured in solution using specific antibodies and the captured IαIp complexes isolated on chip through the capture reagent.

Various methods for quantifying the degree of purification of proteins, polypeptides, or peptides will be known to those of skill in the art in light of the present disclosure. These include, for example, determining the specific protein activity of a fraction, or assessing the number of polypeptides within a fraction by gel electrophoresis.

In addition to those techniques described in detail herein below, various other techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite, lectin affinity, immunoaffinity chromatography and other affinity chromatography steps; isoelectric focusing; gel electrophoresis, HPLC; and combinations of such and other techniques. Furthermore, if viewed as desirable, additional purification steps can be employed using approaches that are standard in this art. These approaches are fully able to deliver a highly pure preparation of the protein.

In other embodiments, gel chromatography, or molecular sieve chromatography may be used. Gel chromatography is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

In other embodiments, affinity chromatography may be used. Affinity chromatography is a chromatographic procedure that relies on the specific affinity between a substance to be isolated and a molecule that it can specifically bind to. This is, for example, a receptor-ligand type interaction. The column material may be synthesized by covalently coupling one of the binding partners to an insoluble matrix. The column material may then be able to specifically adsorb the substance from the solution. Elution occurs, for example, by changing the conditions to those in which binding will not occur (e.g., alter pH, ionic strength, and temperature.).

The methods described herein are amenable for large-scale production, and result in proteins including, the IαIp complex and H4 in a form suitable for therapeutic administration.

Any of the isolation or purification steps of the processes described herein may be repeated to obtain a higher degree of purity, if desired. The chromatography steps may be in batch or in column format.

Preferred processes for producing a blood plasma-derived IαIp composition of the invention include isolating from blood plasma a plasma fraction containing IαI and PαI, wherein the IαI and PαI are present in a physiological proportion; and purifying the plasma fraction to obtain an IαIp composition with a purity of from between about 85% to about 100% pure.

Processes according to the invention may also include further purification of the plasma fraction, for example, by passing to a heparin affinity column and collecting the flow through (unbound) fraction.

Processes useful in practicing the invention may also include virus inactivating the plasma fraction and/or the purified IαIp before and/or after the purification and isolation steps. Typical processes include virus inactivating by a solvent/detergent treatment or thermal inactivation. Thermal inactivations, or pasteurization of the compositions of the invention may be for example at a temperature of between about 55° to about 65° C. or dry heat at 70 to 120° C.

For solvent detergent treatments, a specific combination of solvent and detergents, such as, 0.3% tri-n-butylphosphate (TnBP) combined with 1% Tween-80, at 24° C. for 6 hours, is effective to inactivate enveloped viruses (Horowitz et al (1985) Transfusion 25, pp. 516-522). Alternatively, pasteurization of the fraction or purified IαIp at 55-65° C. in the presence of stabilizers may be sufficient to inactivate any viruses present.

During the purification or isolation step(s) stabilizers may be added. The final composition of IαIp may also contain stabilizers. For example, suitable stabilizers include albumin, polyethylene glycol, alpha, alpha-trehalose, amino acids, salts, glycerol, omega-amino acids such as lysine, polylysine, arginine, epsilon amino caproic acid and tranexamic acid, sugars, such as sucrose, or combinations thereof.

The IαIp proteins and compositions of the invention may be used to treat a human disease. Such diseases include, for example, acute inflammatory diseases, sepsis, severe shock, septic shock, rheumatoid arthritis, cancer, cancer metastasis, preterm labor and infectious diseases. The IαIp compositions used to treat disease may be made by isolating from blood plasma a plasma fraction containing IαI and PαI, wherein the IαI and PαI are present in a physiological proportion; and purifying the plasma fraction to obtain an IαIp composition with a purity of IαIp ranging from about 85% to about 100% pure.

The invention also encompasses pharmaceutical compositions of IαIp. Pharmaceutical compositions of IαIp may be any of the IαIp compositions described herein in a therapeutically effective amount with a pharmaceutically acceptable carrier.

For example, a pharmaceutical composition according to the invention may be a therapeutically effective amount of an IαIp composition which is a mixture of inter-alpha inhibitor protein (IαI) and pre-alpha protein (PαI), wherein the IαI and the PαI are present in said mixture in a physiological proportion ranging from about 85% to about 100% pure. A pharmaceutical composition may also be a therapeutically effective amount of an IαIp composition which is a mixture of inter-alpha inhibitor protein (IαI) and pre-alpha protein (PαI), wherein the IαI and the PαI are present in said mixture in a physiological proportion comprising a light chain of inter-alpha inhibitor protein associated with at least one of three heavy chains H1, H2 and H3 or H1, H2, H3 and H4. A pharmaceutical composition may also be a therapeutically effective amount of an IαIp composition which is a mixture of inter-alpha inhibitor protein (IαI) and pre-alpha protein (PαI), wherein the IαI and the PαI are present in said mixture in a physiological proportion and having a high trypsin inhibitory specific activity. A pharmaceutical composition may also be a therapeutically effective amount of an IαIp composition which is a mixture of inter-alpha inhibitor protein (IαI) and pre-alpha protein (Pa), wherein the IαI and the PαI are present in said mixture in a physiological proportion and having a half life of greater than one hour, five hours, or ten hours.

The term "pharmaceutically acceptable carrier or adjuvant" refers to a carrier or adjuvant that may be administered to a subject, together with a composition of this invention, and which does not destroy the pharmacological activity thereof and is nontoxic when administered in doses sufficient to deliver a therapeutic amount of the composition.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compositions described herein.

The pharmaceutical compositions of this invention may be administered orally, parenterally, by inhalation spray, topically, rectally, nasally, buccally, vaginally or via an implanted reservoir, preferably by oral administration or administration by injection.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated composition or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques. Suitable methods of administration may be as a tablet, capsule, or by intravenous injection. Injectable forms of administration are particularly preferred.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a composition of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compositions of this invention include, but are not limited to, mineral oil, liquid petroleum, white petroleum, propylene glycol, polyoxyethylene polyoxypropylene composition, emulsifying wax and water. Alternatively, the pharmaceutical composition can be formulated with a suitable lotion or cream containing the active composition suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Methods of treating an inflammation related disorders, for example, rheumatoid arthritis, septic and septic shock, head trauma/injury and meningitis, inflammatory bowel diseases (Crohn's Disease), chronic obstructive pulmonary disease, rhinitis; cancer, preterm labor, or an infectious disease in a subject according to the invention may include administering a therapeutically effective amount of an IαIp composition that is produced according to the methods of the invention.

Compositions herein are administered in a dosage ranging from about 1 to 50 mg/kg of body weight, preferably dosages between 500 mg and 1000 mg/dose, every 4 to 120 hours, or according to the requirements of the particular drug. The methods herein contemplate administration of an effective amount of composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active composition (w/w). Alternatively, such preparations contain from about 20% to about 80% active composition.

Lower or higher doses than those recited above may be advantageous. Specific dosage and treatment regimens for any particular subject will depend upon a variety of factors, including the activity of the specific composition employed, the age, body weight, general health status, sex, diet, time of administration, rate of excretion, drug combination, the severity and course of the disease, condition or symptoms, the subject's disposition to the disease, condition or symptoms, and the judgment of the treating physician.

Upon improvement of a condition, a maintenance dose of a composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Subjects may, however, require intermittent treatment on a long-term basis upon any recurrence of disease symptoms. Improvement of the condition may also be judged based upon the level of I$\alpha$Ip in the liver. If normal physiological levels of I$\alpha$Ip are found in the liver and the patients symptoms as judged by the subject or the treating physician are judged to be improved, the subject may treated with a maintenance dose.

When the compositions of this invention comprise a combination of an I$\alpha$Ip composition and one or more additional therapeutic or prophylactic agents, both the composition and the additional agent should be present at dosage levels of between about 1 to 100%, and more preferably between about 5 to 95% of the dosage normally administered in a monotherapy regimen. The additional agents may be administered separately, as part of a multiple dose regimen, from the compositions of this invention. Alternatively, those agents may be part of a single dosage form, mixed together with the compositions of this invention in a single composition.

Methods for treating a subject for acute inflammatory disease, sepsis, severe shock, septic shock, rheumatoid arthritis, cancer, cancer metastasis, infectious disease, and/or preterm labor, include the steps of determining the pre-treatment level of one or more of I$\alpha$I, P$\alpha$I, I$\alpha$Ip, H3, H4, H1, H2, and LC; and administering a therapeutically effective amount of I$\alpha$Ip to the subject. Pre-treatment levels of I$\alpha$I, P$\alpha$I, I$\alpha$Ip, H3, H4, H1, H2, and LC are the levels of the proteins in the subject prior to the first administration of I$\alpha$Ip or any of the I$\alpha$Ip complex proteins. Post-treatment levels are the levels of I$\alpha$Ip measured after administration of I$\alpha$Ip. The methods of the invention include determining the post-treatment levels of one or more of I$\alpha$I, P$\alpha$I, I$\alpha$Ip, H3, H4, H1, H2, and LC after an initial period of treatment with I$\alpha$Ip. A modulation in the level of I$\alpha$Ip is an indication that the treatment is producing a favorable clinical response. The initial period of treatment may be the time required to achieve a steady-state plasma concentration of the I$\alpha$Ip.

The level of I$\alpha$I, P$\alpha$I, I$\alpha$Ip, H3, H4, H1, H2, and/or LC may be determined, for example, by immunological methods. For example, I$\alpha$Ip complexes can be detected and/or measured by a variety of detection methods including for example, gas phase ion spectrometry methods, optical methods, electrochemical methods, atomic force microscopy, radio frequency methods, surface plasmon resonance, ellipsometry immunological, and atomic force microscopy methods.

In another embodiment, an immunoassay can be used to detect and analyze I$\alpha$Ip complexes in a sample. This method comprises: (a) providing an antibody that specifically binds to an I$\alpha$Ip complex; (b) contacting a sample with the antibody; and (c) detecting the presence of a complex of the antibody bound to the I$\alpha$Ip complex in the sample. Suitable antibodies for use in the methods of the invention include, MAb 69.31, MAb 69.26, anti-I$\alpha$Ip polyclonal antibody (R16 or R20), and anti-bikunin monoclonal or polyclonal antibody.

An immunoassay is an assay that uses an antibody to specifically bind an antigen (e.g., an I$\alpha$Ip complex). The immunoassay is characterized by the use of specific binding properties of a particular antibody to isolate, target, and/or quantify the antigen. The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to an I$\alpha$Ip complex from specific species such as rat, mouse, or human can be selected to obtain only those polyclonal antibodies that are specifically immunoreactive with that I$\alpha$Ip complex and not with other proteins, except for polymorphic variants and alleles of the I$\alpha$Ip complex. This selection may be achieved by subtracting out antibodies that cross-react with the I$\alpha$Ip complex molecules from other species.

Subjects suitable for treatment with I$\alpha$Ip may be identified as having inflammation, trauma/injury, tumor invasion, tumor metastasis, sepsis, septic shock, or an infectious disease. The subject may be self-identified or diagnosed by a medical practitioner as having inflammation, tumor invasion, tumor metastasis, sepsis, septic shock, or an infectious disease. The subjects may be primates, humans, or other animals.

Methods also include the co-administration of other therapeutic agents. For example, the additional therapeutic agents may be anticancer agents, anti-inflammatory agents, anticoagulants or immunomodulators. For example, dideoxynucleosides, e.g. zidovudine (AZT), 2',3'-dideoxyinosine (ddI) and 2',3'-dideoxycytidine (ddC), lamivudine (3TC), stavudine (d4T), and TRIZIVIR (abacavir+zidovudine+lamivudine), nonnucleosides, e.g., efavirenz (DMP-266, DuPont Pharmaceuticals/Bristol Myers Squibb), nevirapine (Boehringer Ingleheim), and delaviridine (Pharmacia-Upjohn), TAT antagonists such as Ro 3-3335 and Ro 24-7429, protease inhibitors, e.g., indinavir (Merck), ritonavir (Abbott), saquinavir (Hoffmann LaRoche), nelfinavir (Agouron Pharmaceuticals), 141 W94 (Glaxo-Wellcome), atazanavir (Bristol Myers Squibb), amprenavir (GlaxoSmithKline), fosamprenavir (GlaxoSmithKline), tipranavir (Boehringer Ingleheim), KALETRA (lopinavir+ritonavir, Abbott), and other agents such as 9-(2-hydroxyethoxymethyl)guanine (acyclovir), interferon, e.g., alpha-interferon, interleukin II, and phosphonoformate (Foscarnet), or entry inhibitors, e.g., T20 (enfuvirtide, Roche/Trimeris) or UK-427,857 (Pfizer), levamisol or thymosin, cisplatin, carboplatin, docetaxel, paclitaxel, fluorouracil, capecitabine, gemcitabine, irinotecan, topotecan, etoposide, mitomycin, gefitinib, vincristine, vinblastine, doxorubicin, cyclophosphamide, celecoxib, rofecoxib, valdecoxib, ibuprofen, naproxen, ketoprofen, dexamethasone, prednisone, prednisolone, hydrocortisone, acetaminophen, misonidazole, amifostine, tamsulosin, phenazopyridine, ondansetron, granisetron, alosetron, palonosetron, promethazine, prochlorperazine, trimethobenzamide, aprepitant, diphenoxylate with atropine, and/or loperamide. Anti-coagulants such as Anti-thrombin III, activated Protein C and protease inhibitors such as furin inhibitors Methods also include predicting a response to an IαIp therapy by assaying a sample obtained from a subject to detect the level of one or more of IαI, PαI, IαIp, H3, H4, H1, H2, and LC; wherein the detected levels identifies a subject that may respond favorably to IαIp therapy. For example, a decrease in a detectable level of IαI and/or PαI indicates that a subject may benefit from the administration of IαIp.

Methods also include monitoring the progress of a subject being treated with an IαIp therapy by determining the pre-treatment level of one or more of IαI, PαI, IαIp, H3, H4, H1, H2, and LC; administering a therapeutically effective amount of IαIp to the subject; and determining the level of one or more of the levels in the subject after an initial period of treatment with the IαIp, wherein an increase of the level in the subject following treatment with IαIp indicates that the subject is likely to have a favorable clinical response to treatment with IαIp.

Kits for IαIp therapy may include one or more of IαI, PαI, IαIp, H3, H4, H1, H2, and LC; and instructions for therapeutic use. Kits are also contemplated that have the IαIp compositions described herein and instructions for use. For example, a kit may have IαI, PαI, and instructions that provide information regarding dosage, form of administration, and storage conditions.

A container including IαIp and a label or package insert with instructions for administering the IαIp to a subject are also contemplated. The instructions may provide instructions for dosage, form of administration, and storage conditions.

EXAMPLES

It should be appreciated that the invention should not be construed to be limited to the examples which are now described; rather, the invention should be construed to include any and all applications provided herein and all equivalent variations within the skill of the ordinary artisan.

Example 1

Characterization of H4 as a Part of the IαIp Complex

SELDI-TOF mass spec analysis indicated that heavy chain 4 (H4) is also present in both 125 kDa band (PαI) and 250 kDa band (IαI) (data not shown). The presence of H4 in the 250 kDa band is more pronounced. This suggests that another complex protein other than IαI (H1+H2+LC) and PαI (H3+LC) might be present in some compositions of the invention. So far, H4 has not been described in the complexed form. Free H4 is smaller than 125 or 250 kDa. Due to the mass spec results, we think that H4 might be in complex with bikunin (the light chain) or something else.

Example 2

Animal Model of Sepsis

Male Sprague-Dawley rats (275-325 g) were housed in a temperature-controlled room on a 12-h light/dark cycle and fed a standard Purina rat chow diet. Prior to the induction of sepsis, rats were fasted overnight but allowed water ad libitum. Rats were anesthetized with isoflurane inhalation and the ventral neck, abdomen and groin were shaved and washed with 10% povidone iodine. A 2-cm midline abdominal incision was performed. The cecum was exposed, ligated just distal to the ileocecal valve to avoid intestinal obstruction, punctured twice with an 18-gauge needle, squeezed slightly to allow a small amount of fecal matter to flow from the holes, and returned to the abdominal cavity; the abdominal incision was then closed in layers. Sham-operated animals (i.e., control animals) underwent the same procedure with the exception that the cecum was neither ligated nor punctured. The animals were resuscitated with 3 ml/100 g BW normal saline subcutaneously immediately after surgery. Animals were then anesthetized at various intervals after cecal ligation and puncture (CLP) or sham operation for collection of tissue samples. All experiments were performed in accordance with the National Institutes of Health guidelines for the use of experimental animals. This project was approved by the Institutional Animal Care and Use Committee of the North Shore-Long Island Jewish Research Institute.

Preparation and Administration of Human IαIp

Human IαIp (both IαI and PαI) was isolated as a by-product of a procedure designed for purifying coagulation factor VIII from human plasma. The procedure involves ion exchange and size-exclusion chromatography of cryoprecipitates. A purity of approximately 70% was achieved after the chromatographic separation. This IαIp containing preparation has few side effects in terms of toxicity, thrombogenicity, or hypotension. At 1, 5, 10 or 10 and 20 h after the onset of sepsis, the left femoral vein was cannulated with a polyethylene-50 tubing under isoflurane anesthesia Human IαIp concentrates at a dose of 30 mg/kg BW or an equivalent volume of vehicle (normal saline, 1.5 ml/rat) were administered intravenously via the femoral catheter over 30 min at a constant infusion rate. Administration of human IαIp, in previous experiments, did not alter mean arterial pressure or heart rate during the period of infusion or thereafter (data not shown).

RNA Extraction and Determination of Hepatic Bikunin Genes

The liver may be the major source of bikunin. Therefore, we measured bikunin mRNA expression in the liver. Total RNA was extracted from the liver by Tri-Reagent (Molecular Research Center, Cincinnati, Ohio). One hundred mg of liver tissue was homogenized in 1.5 ml Tri-Reagent, separated into aqueous and organic phases by chloroform addition, and centrifuged. RNA was precipitated from the aqueous phase by addition of isopropanol, and washed with ethanol. The pellet was dissolved in 0.1% DEPC-treated, deionized distilled water. RNA concentration and purity were determined by measuring the absorbance at 260 and 280 nm. Five μg of RNA from each tissue was reverse-transcribed in a 20 μl reaction volume containing 50 mM KCl, 10 mM Tris-HCl, 5 mM MgCl2, 1 mM dNTP, 20 U RNase inhibitor, 2.5 mM oligo d(T) 16 primer and 50 U reverse transcriptase. The reverse transcription reaction solution was incubated at 42° C. for 1 h, followed by heating at 95° C. for 5 min. One μl cDNA was amplified with 0.15 μM each of 3' and 5' primers, specific for rat bikunin (633 bp) (5' TGA CGA ATA TGC CAT TTT CC 3', 5'CCA CAG TAC TCC TTG CAC TCC 3') (accession No.

S87544), rat glyceraldehydes-3-phosphate-dehydrogenase 7 (G3PDH) (24) (983 bp) (5' TGA AGG TCG GTG TCA ACG GAT TTG GC 3', 5'CAT GTA GGC CAT GAG GTC CAC CAC 3') in 25 μl of PCR mixture containing 50 mM KCl, 10 mM Tris-HCl, 2 mM MgCl2, 0.2 mM dNTP and 0.7 U Ampli-Taq DNA polymerase. PCR was carried out in a Bio-Rad thermal cycler. Following RT-PCR, 5 μl of the reaction mixture was electrophoresed in 1.2% TBE-agarose gel containing 0.22 μg/ml ethidium bromide. The gel was then developed and band intensities were normalized by G3PDH using the Bio-Rad image system (Hercules, Calif.).

Radioiodination of Protein and Determination of IαIp Half-Life

Purified IαIp was radioiodinated with Na$^{125}$I (Amersham, Arlington Heights, Ill.) using 1,3,4,6-tetrachloro-3a-6a-diphenyl glycoluril (IODO-GEN iodination reagent; Pierce, Rockford, Ill.). The unincorporated $^{125}$I was removed by applying the reaction mixture to an Excellulose GF-5 desalting column (Pierce). Radioactivity was determined in a gamma counter (Pharmacia-LKB, Piscataway, N.J.). At 12 h after CLP or sham operation, the animals were anesthetized with isoflurane inhalation. A steady state of sedation was maintained with a subsequent intravenous injection of sodium pentobarbital (~30 mg/kg BW). Polyethylene-50 catheters were placed in the right jugular vein and left femoral artery, and a bolus injection of $^{125}$I-labeled IαIp (~500,000 cpm/rat) was administered through the jugular cannula. The remaining radioactivity in the syringe was measured with a gamma counter, and the radioactivity counts were subtracted from the initial preinjection counts to determine the net injected radioactivity. Blood samples were collected immediately after the injection and then every 2 h for a period of 8 h for determining the half-life ($t_{1/2}$) of $^{125}$I-IαIp in the circulation. The radioactivity (cpm) in each sample was measured with a gamma counter. The $t_{1/2}$ was calculated according to Wu R, Zhou M, Cui X, et al: Ghrelin clearance is reduced at the late stage of polymicrobial sepsis. *Int J Mol Med.* 2003; 12:777-782.

Survival Study

CLP was performed as described above. At 1, 5, 10 or 10 and 20 h after CLP, human IαIp concentrate (30 mg/kg BW) or vehicle (normal saline, 1.5 ml/rat, at 1 h after CLP or 10 and 20 h after CLP) was infused intravenously. At 20 h after CLP, the necrotic cecum was excised and the abdominal cavity was washed twice by using 40 ml of warm, sterilized normal saline solution. The abdominal incision then was closed in layers. The procedure of cecal excision in CLP animals was performed to mimic the clinical situation in which septic focus should be removed whenever possible. The animals then were allowed food and water ad libitum and were monitored for 10 days to record survival.

Statistical Analysis

Results are expressed as means ±SE. One-way analysis of variance (ANOVA) and Tukey's test were used to compare different groups of experimental animals. The survival rate was estimated by Kaplan-Meier method and compared by the log-rank test. Differences in values were considered significant if P<0.05. 9

Alterations in Bikunin mRNA Expression after CLP

Bikunin is an active part of IαIp. The liver is the major source of bikunin. Therefore, we chose bikunin mRNA expression in the liver to reflect the production of IαIp. As shown in FIG. 3, mRNA expression of bikunin in the liver did not change at 5 h after CLP, however, a 32% decrease was found at 20 h after CLP as compared with sham operated animals (P<0.05).

Alterations in $t_{1/2}$ of $^{125}$I-IαIp after CLP

Half-life of IαIp was estimated by measuring the changes of blood levels of radioactive labeled IαIp injected at 12 h after the onset of sepsis. As indicated in FIG. 4, the $t_{1/2}$ of 125I-IαIp was significantly increased from 5.6±0.3 h to 11.8±2.7 h (P<0.05) after CLP.

Effects of IαIp on Survival Rate

Figure 5:
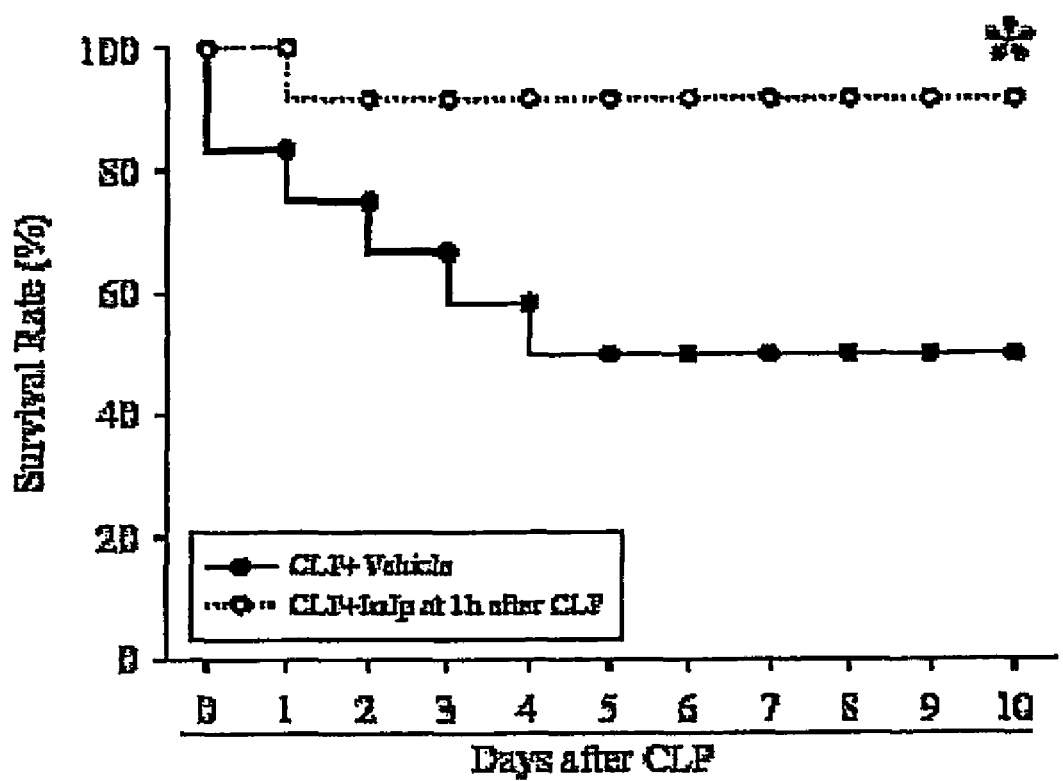
FIG. 5 depicts the alterations in the survival rate at 10 days after cecal ligation and puncture and cecal excision with vehicle treatment (CLP+Vehicle) and cecal ligation and puncture with inter-α-inhibitor treatment (CLP+IαIp). There were 12 animals in each group. The survival rate was estimated by the Kaplan-Meier method and compared by using the log-rank test * P<0.05 vs. CLP+Vehicle.
Figure 6:
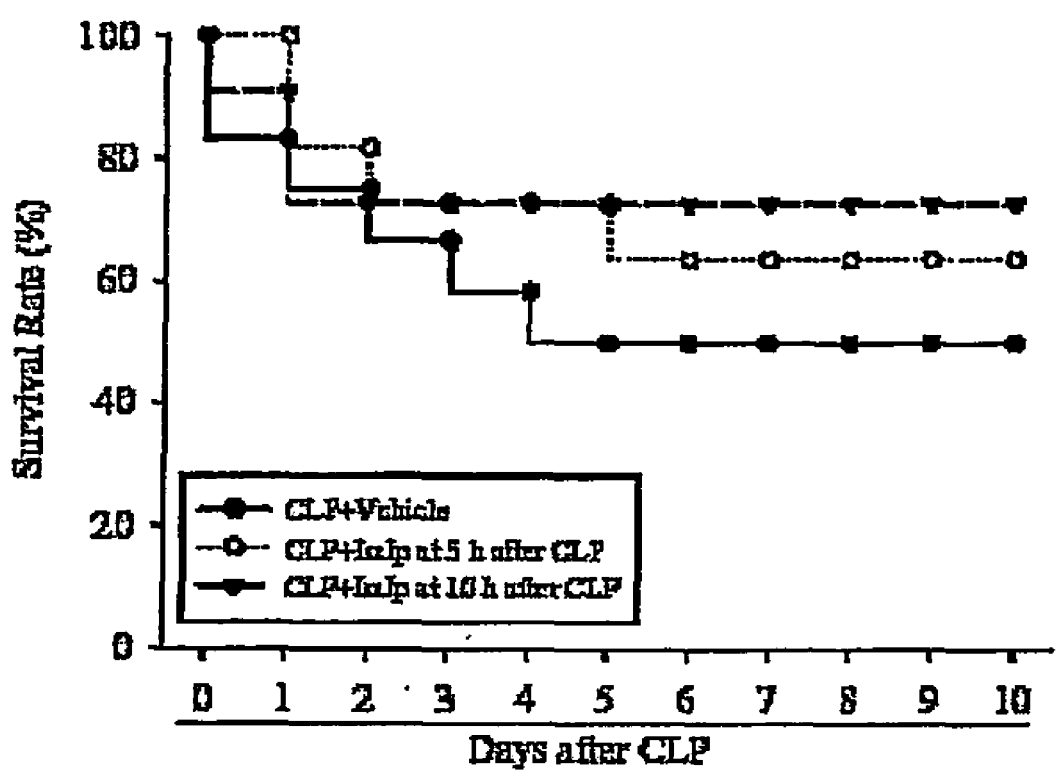
FIG. 6 depicts the alterations in the survival rate at 10 days after cecal ligation and puncture and cecal excision with vehicle treatment (CLP+Vehicle) and cecal ligation and puncture with inter-α-inhibitor treatment (CLP+IαIp). There were 11 to 12 animals in each group. The survival rate was estimated by the Kaplan-Meier method and compared by using the log-rank test. * P<0.05 vs. CLP+Vehicle.
Figure 7:
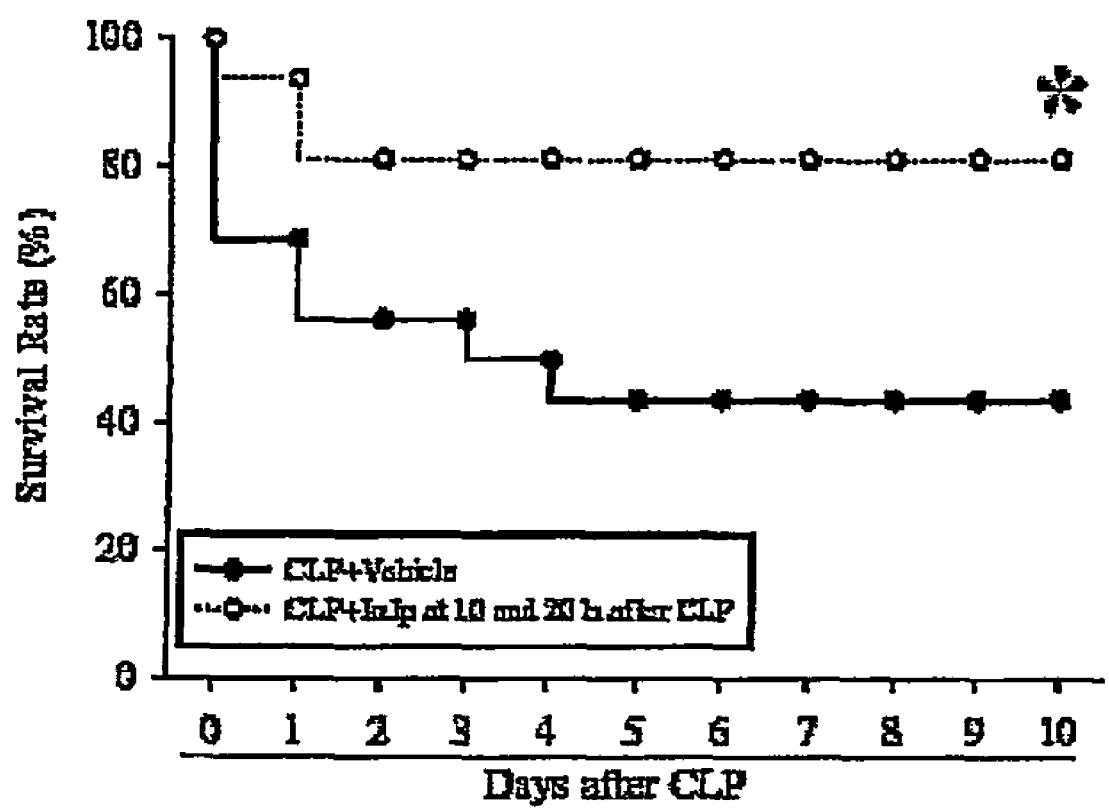
FIG. 7 describes alterations in the survival rate at 10 days after cecal ligation and puncture and cecal excision with vehicle treatment (CLP+Vehicle) and cecal ligation and puncture with inter-α-inhibitor treatment (CLP+IαIp). There were 16 animals in each group. The survival rate was estimated by the Kaplan-Meier method and compared by using the log-rank test. * P<0.05 vs. CLP+Vehicle.

The survival rate after CLP and cecal excision with single time vehicle administration (at 1 h after CLP) was 75% at day 2 and decreased to 50% at days 5-10 FIG. 5). Administration of human IαIp at 1 h after CLP, however, improved the survival rate to 92% throughout the 10-day observation period (P<0.05; FIG. 5). Although administration of human IαIp at 5 or 10 h after CLP improved the survival rate to 64% and 73% respectively, these improvements were not statistically significant (FIG. 6). The survival rate after CLP and cecal excision with two times vehicle administration (at 10 and 20 h after CLP) was 56% at day 2 and decreased to 44% at days 5-10 (FIG. 7), which was not significantly different as compared with one time vehicle administration (FIG. 5). Administration of human IαIp at 10 and 20 h after CLP, however, improved the survival rate to 81% throughout the 10-day observation period, which was significantly different as compared with vehicle group (P<0.05; FIG. 7).

Sepsis is a clinical syndrome characterized by systemic inflammation, coagulopathy, respiratory failure, myocardial dysfunction, renal insufficiency, and neurocognitive defects. It is generally assumed that this syndrome results from an excessive triggering of endogenous inflammatory mediators by the invading microorganisms. These mediators include substances released by activated monocytes, macrophages, endothelial cells and neutrophils such as cytokines, reactive oxygen species and proteases. In severe inflammatory response, various blood and tissue cells, including polymorphonuclear granulocytes, release lysosomal proteinases extracellularly and into the circulation. Such proteases as well as normally intracellular oxidizing agents produced during phagocytosis, can trigger tissue and organ damage and enhance the nonspecific proteolysis of plasma clotting and complement factors. The release of neutrophil proteinases, especially human leukocyte elastase, has been implicated in the progress of complications in subjects with sepsis. Their plasma levels are in close correlation with the severity of infection-induced inflammation and highly predictive of forthcoming organ failure.

During septic shock in humans, in addition to elevated activities of proteases, decreased plasma levels of IαIp have been reported. Subjects with severely decreased concentrations of IαIp have a higher mortality rate. Our results indicate that the gene expression of bikunin in the liver is significantly lower in the CLP animals than in the sham-operated animals. The expression of mRNA related to proteins in the inter-alpha-inhibitor family has been examined in various tissues in primates, pigs, and rodents. These studies indicate the genes which are the source of all members of the IαIp family are primarily transcribed in the liver. Our results also show the gene expression of bikunin in other organs (i.e., intestine and kidneys) was not significantly altered at 5 or 20 h after CLP as compared to the shams (data not shown).

The significant downregulation observed only in the liver at 20 h after CLP suggests that this organ might be an important source of IαIp and furthermore, in late stages of sepsis, bikunin gene expression in the liver is significantly decreased. Therapeutically, bikunin has been reported to have beneficial effects in humans as a prophylactic treatment to prevent pancreatitis after gastrectomy or to attenuate organ injury after cardiac surgery. Studies that examined the effects of bikunin in an acute canine model of lethal *E. coli* bacteremia showed similar results with an improvement in hemodynamic variables and normalization of cardiac output and mean arterial pressure. Because the plasma half-life of bikunin is very short (approximately 10 min), it appears important to prolong the half-life of bikunin to maintain the sustained beneficial effects of this agent. Our results show that the half-life of IαIp in sham-operated animals is 5.6 h. When we injected radioactive labeled IαIp at 12 h after the onset of sepsis, we found the half-life of IαIp was prolonged to 11.8 h. These results indicate that IαIp clearance was significantly decreased during sepsis. However, even with decreased clearance the plasma levels of IαIp remain significantly lower in septic subjects. Our previous study has shown that administration of low purity IαIp early after the onset of sepsis (i.e., 1 h post-CLP) maintained cardiac output and systemic oxygen delivery and increased systemic oxygen consumption and systemic oxygen extraction ratio. Moreover, IαIp downregulated TNF-a production and attenuated hepatocellular injury and lactic acidosis at 20 h after CLP. In addition, IαIp administration at 1 h after the onset of sepsis improved survival in septic animals.

Human IαIp proteins were isolated as a by-product of industrial scale plasma fractionation. The isolation method highly, simultaneously enriches the major plasma form of bikunin-containing proteins (IαI and PαI). Thus, in this preparation, a physiologic composition of plasma IαIp is obtained. The results of the mortality study performed indicate that administration of IαIp at 1 h after CLP improved the survival rate from 50% to 92% at 10 days after CLP and cecal excision. Although administration of human IαIp at 5 or 10 h after CLP improved the survival rate to 64% and 73% respectively, these improvements were not statistically significant.

Administration of human IαIp at 10 and 20 h after CLP, however, significantly improved the survival rate from 44% to 81%. Thus, IαIp appear to be a useful adjunct for improving survival during the progression of polymicrobial sepsis. In summary, bikunin gene expression in the liver decreased during sepsis and the half-life of IαIp increased from 5.6±0.3 h to 11.8±2.7 h, suggesting downregulation of bikunin in sepsis despite a decrease clearance. Administration of IαIp at 1 h after CLP improved the survival rate from 50% to 92%, whereas there was no significant improvement when IαIp was administrated at 5 or 10 h after CLP. However, double injection of IαIp at 10 and 20 h after CLP increased the survival rate from 44% to 81%. Delayed but repeated administration of human IαIp improve survival after CLP.

Example 3

Purification of IαIp

After application of dialyzed or ultra/diafiltrated eluate after solid-phase extraction with DEAE Sephadex A50, weakly bound components are eluted from DEAE-Sepharose FF column with 0.005 M sodium citrate/0.0055 M sodium phosphate buffer, pH 6.0 containing 0.28 M sodium chloride (described in Hoffer et al., Journal of Chromatography B 669 (1995) 187-196). In the previous step, the column was washed with 0.005 M sodium citrate/0.0055 M sodium phosphate buffer, pH 6.0, containing 0.20 M sodium chloride.

After dialysis or ultrafiltration/diafiltration (UF/DF) against 0.005 M sodium phosphate buffer pH 7.0, the eluate was applied to hydroxylapatite column. The IαIp proteins do not bind to the column and are collected as flow through fraction. The contaminating proteins, mainly FII, FVII and FX, can be eluted using a gradient with an increasing concentration of sodium phosphate buffer. The IαI/PαI fraction contains more than 90% of target proteins, mainly IαI and PαI.

Example 4

Purification of IαIp from a Factor IX Flow Through Fraction

Unbound proteins from Heparin Sepharose affinity chromatography (L. Hoffer et al., J. of Chromatography B), are applied to a DEAE-Sepharose FF anion-exchange column. After washing the column with a minimum of three column volumes of 0.005 M phosphate buffer, pH 7.0, IαIp/PαI containing fractions were eluted with 0.005 M phosphate buffer, pH 7.0, containing 0.55 M sodium chloride (elution buffer). The eluate contains about 30-40% IαI/PαI. After dialysis or ultrafiltration/diafiltration (UF/DF) against 0.005 M sodium phosphate buffer, pH 7.0, the eluate from DEAE Sepharose EF was applied to a hydroxylapatite column. The IαI/PαI do not bind to the column and are collected as a flow-through fraction. The contaminating proteins, mainly FII and FX can be eluted using a gradient with increasing concentration of sodium phosphate buffer. The purified IαI/PαI fraction contains more than 90% of the target proteins Example 5

Eluant from a solid-phase extraction of cryopoor plasma on DEAE-Sephadex A50 (L. Hoffer et al., J. of Chromatography B) or Q-Sephadex A50 (D. Josic et al., Thrombosis Research, cf. above) was applied to a DEAC-CIM tube monolith with a column volume of 80 mL (cf. K. Branovic et al., J of Chromatography A, 903 (2000) 21-32). The unbound fraction (flow-through) was collected. The column was subsequently washed with three column volume of 0.02 M Tris-HCl, pH 7.4 (equilibration buffer). Bound proteins were eluted in first step with 0.02 M Tris-HCl, pH 7.4, containing 0.35 Mol/L sodium chloride (Eluate 1) and in a second step with 0.02 M Tris-HCl, pH 7.4, containing 0.55 M sodium chloride (Elution 2). IαI/PαI are found in flow-through fractions and Eluate 1. Flow-through fractions contain about 35-45% IαI/PαI. The amount of these target proteins in Eluate 1 is between 20-30%. Fractions containing IαI/PαI were subjected to dialyses or ultrafiltration/diafiltration (UF/DF) against 0.005 M sodium phosphate buffer, pH 7 and applied to a hydroxylapatite column. IαIp do not bind to the column and are collected as a flow-through fraction. The flow-through fraction contains more than 90% of IαI/PαI.

Figure 8A:
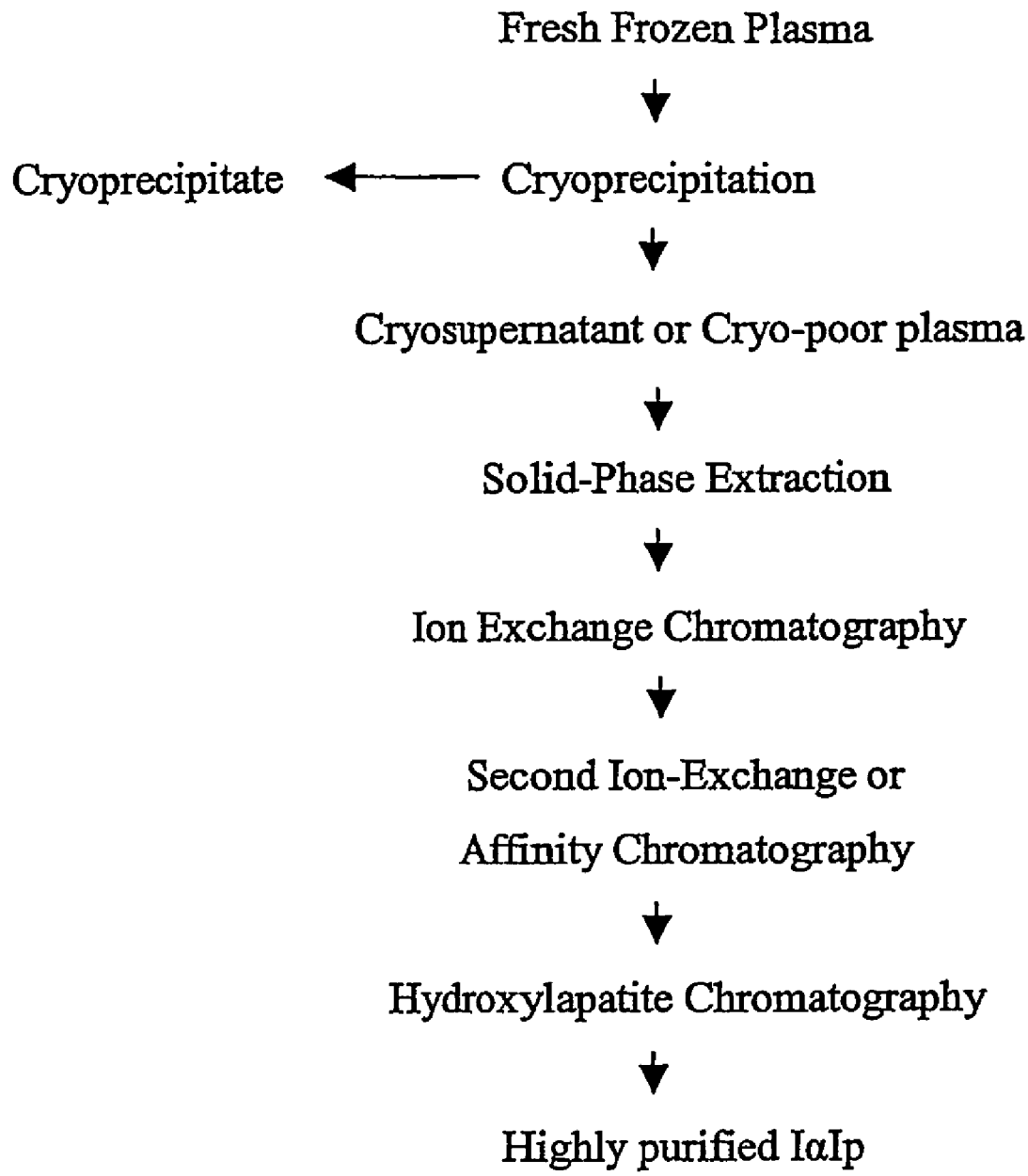
FIGS. 8a and 8b describe purification schemes of IαIp from human plasma, according to the invention.
Figure 8B:
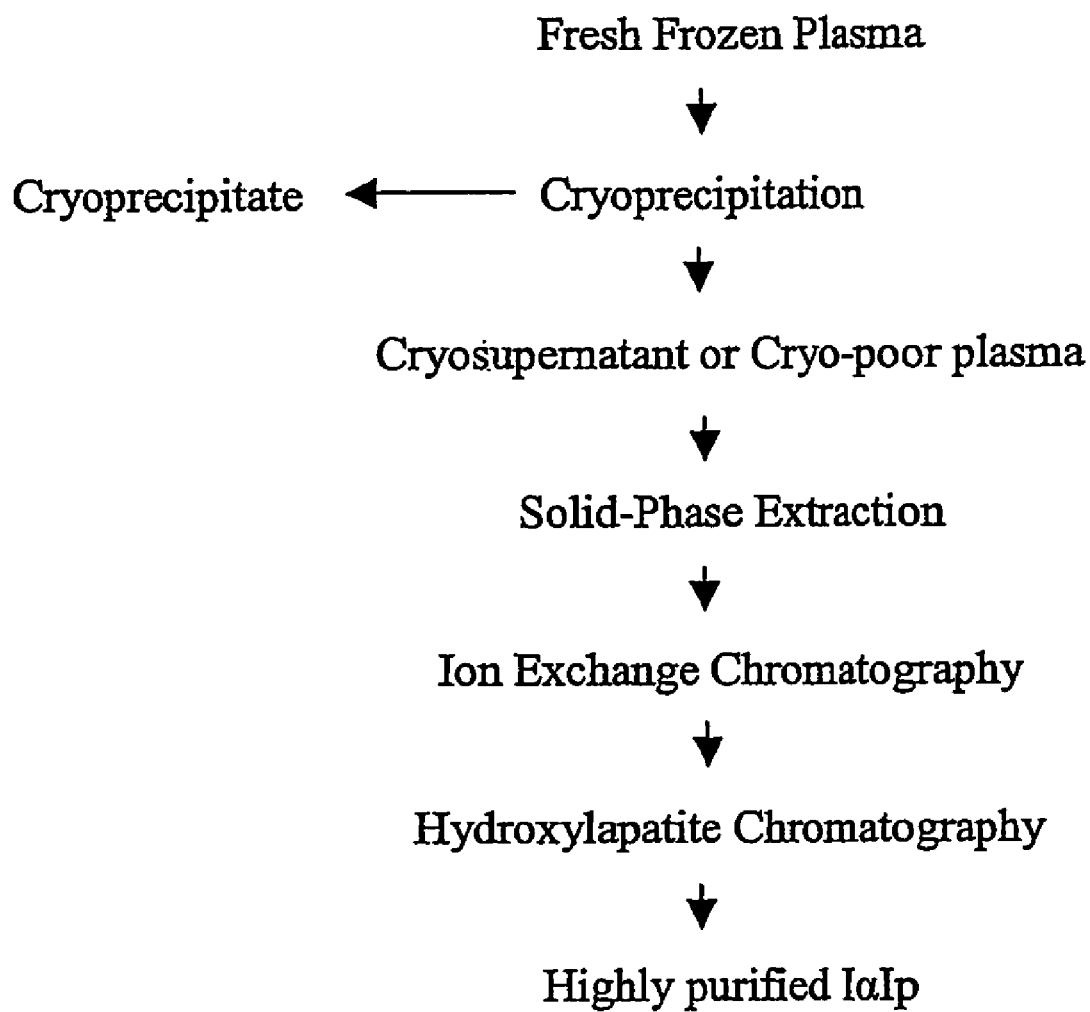

FIGS. 8a and 8b describe exemplary purification schemes of IαIp in a flow diagram as represented by Examples 3-5.

Example 6

Beneficial Effects of Highly Purified IαIp in the Animal Studies

Figure 9:
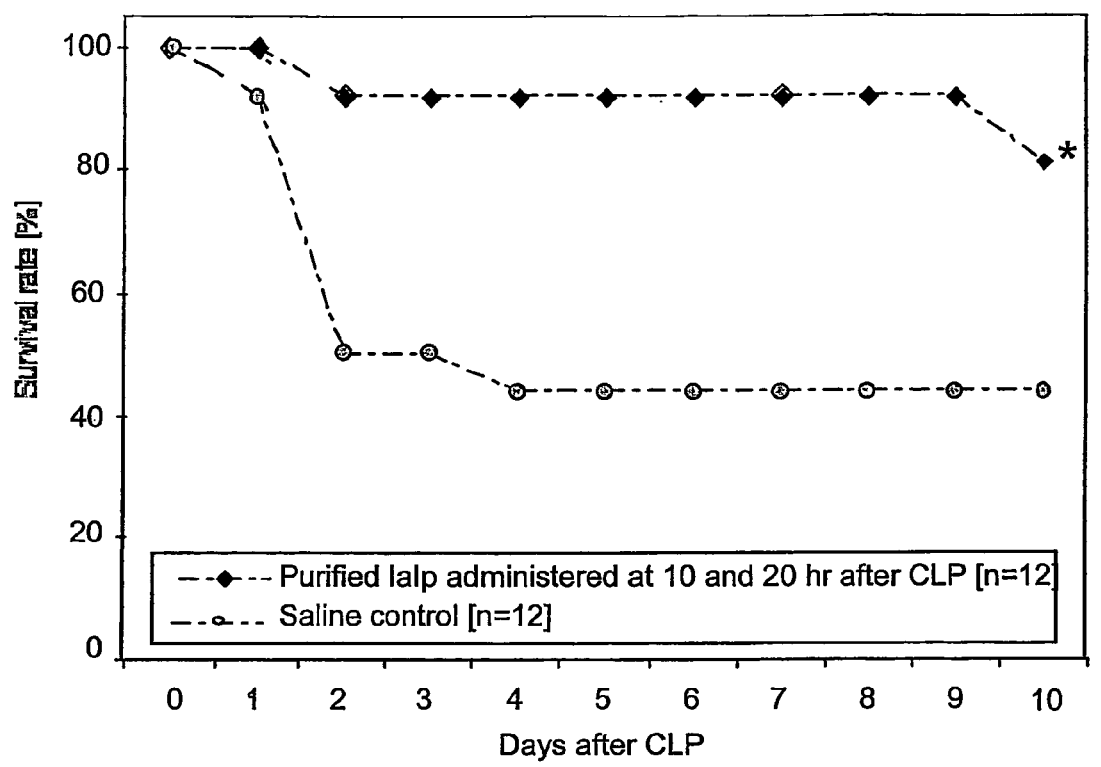
FIG. 9 graphically depicts the beneficial effects of highly purified IαIp in the animal studies of sepsis.

Polymicrobial sepsis was induced by cecal ligation and puncture (CLP) in male Sprague-Dawley rats. Animals were fasted overnight before CLP was performed but were allowed water ad libitum. At the time of the experiment, the rats were anesthetized by methylflurane inhalation, and a 2-cm ventral midline incision was performed. The caecum was exposed, ligated just distally to the ileocecal valve to avoid intestinal obstruction, punctured twice with an 18-gauge needle, squeezed gently to force out a small amount of feces, and then returned to the abdominal cavity. The abdominal incision was closed in layers, and the animals received 30 mL/kg body weight normal saline solution subcutaneously immediately after CLP as a fluid resuscitation. Two groups of rats with n=12 per group were used in this experiment. The treatment group received highly purified IαIp at 10 and 20 hrs after CLP at 30 mg/kg bodyweight. The control group received saline. At 20 hr after CLP, the necrotic caecum was excised and the abdominal cavity washed twice by using 40 mL of warm, sterile normal saline solution. The abdominal incision was then closed in layers. The procedure of cecal excision in CLP animals was performed to mimic the clinical situation in which the septic focus is removed. The experimental animals were allowed food ad libitum and monitored for 10 days to record the time of death for the non-survivors. A log-rank test was employed for comparison of mortality rates among different groups of animals and p values were determined by Kaplan-Meier method. A significant increase in survival was observed in the treatment group compared to the saline control group (81.3% of the animals in the treatment group survived vs. 44% in the control group (p value=0.0293)), suggesting that the highly purified IαIp is biologically active and effective in reducing the sepsis-related death in septic animals. Results are shown in FIG. 9.

TABLE 1

Comparison of the specific inhibitory activity of IαIp

| IαIp preparation Purified from | Protein conc. [mg/mL] | IαIp conc. [mg/mL] | IαIp purity [%] | Specific Inh. Activity [TIU/mg IαIp] |
|---|---|---|---|---|
| Cryoprecipitate | 7.30 | 5.10 | 69.86% | 1412 ± 47.52 |
| Cryopoor plasma | 17.30 | 17.00 | 98.27% | 1409 ± 42.50 |

TIU = Trypsin inhibitory unit; mean ± SD from three independent experiments.

Specific inhibitory activity of the highly purified IαIp (from cryo-poor plasma) was calculated and compared with IαIp purified from the cryoprecipitate, a side-fraction of fVIII production. The biological activity of IαIp was measured in a trypsin inhibition assay using the chromogenic substrate L-BAPA (N(alpha)-Benzoyl-L-arginine-4-nitroanilide hydrochloride (Fluka Chemicals). This assay is based on the ability of IαIp to inhibit the hydrolysis of L-BAPA. Inhibition can be monitored by a decrease in the rate of Δ absorbance/minute at 410 nm. Total protein concentration was quantitatively measured by the BioRad protein assay and IαIp concentrations were measured using a competitive ELISA using MAb 69.31 as described in Lim et al, J. of Infectious Diseases, 2003). There was no significant difference in the specific trypsin inhibitory activity between IαIp preparations purified from cryo-poor plasma and cryoprecipitate (p value=0.939), suggesting that IαIp in both fractions had comparable biological activity.

Example 7

Side Fraction from FIX Purification

The "washing fraction" from the chromatographic purification of clotting factor FIX on DEAE-Sepharose FF (Josic et al. Journal of Chromatography, cited above). This fraction can be eluted with a 0.01-0.1 M sodium citrate/0.005-0.1 M sodium phosphate buffer, pH 6.0 containing 0.25 M sodium chloride. The IαI and PαI are the main components in this fraction. The FIX containing fraction can be eluted from DEAE Sepharose FF column with a 0.01-0.1 M sodium citrate/0.005-0.1 M sodium phosphate buffer, pH 6.0 containing 0.3-0.6 M sodium chloride in the next step. This fraction also contains other vitamin K dependent clotting factors such as clotting factor II (FII), clotting factor X (FX), lower amounts of clotting factor VII (FVII) together with residual amounts of IαIp. After dialysis to reduce osmolarity and salt concentration, the residual IαIp in the FIX fraction can be recovered by affinity chromatography on immobilized heparin and step elution in buffers with increasing salt concentration and osmolality. Fractions from an early elution step in the wash buffer contain over 80% IαIp with very low FIX contamination. Elution of FIX occurs at a later step in a buffer with higher salt concentration and osmolality. There is also a flow through fraction that does not bind to heparin, is free of FIX and contains a mixture of IαIp (30-40%), vitamin K-dependent clotting factors, and the solvent/detergent (S/D) used for virus inactivation. The S/D can be removed in an additional chromatographic step of DEAE-Sepharose FF.

IαIp containing fractions collected from DEAE-Sepharose, immobilized heparin or the flow through from heparin can be further purified individually or as a pool by hydroxylapatite chromatography. Using either approach, the final preparation contains more than 90% ITI.

The concentrate purified using these protocols contains more than 90% IαI/PαI. It has been virus inactivated by solvent/detergent treatment. Terminal heating in final container with or without use of stabilizers for more than 30 minutes or pasteurization at 55-65° C. in the presence of stabilizers can be introduced as a second virus inactivation step without significant loss of activity.

The resulting concentrate containing more than 90% IαI/PαI can be virus inactivated with S/D treatment or as a second inactivation step, terminal heating of the purified proteins with or without stabilizers for 30 minutes or alternatively, pasteurization at 55-65° C. in the presence of stabilizers.

A Strong Anion-Exchange Fraction

Instead of the eluate after solid-phase extraction with weak anion-exchanger DEAE Sephadex A50) an eluate after solid phase extraction with a strong anion-exchanger Q Sephadex A50 can be used. Conditions for elution are described in German patent DE 4342132C1. A mixture of IαI and PαI do not bind or only weakly binds to the monolithic anion-exchange support DEAE-CIM. Other proteins such as clotting factors FII, FVII, FIX and FX, clotting inhibitors PC, PS and PZ, adhesion protein vitronectin and protease FSAP are eluted in separate fractions. Further separations of the remaining contaminants can be achieved in the next step using hydroxylapatite chromatography.

A Monolith Chromatographic Fraction

A DEAE CIM monolith (membrane) can be used for chromatographic separation in FIX purification instead of DEAE Sepharose FF or other particle-based anion exchanger (See DE 4342132C1). Surprisingly, IαI and PαI did not bind or bound only weakly to the monolithic support. Other proteins, such as FIX, vitronectin and FII, FVII (low amount) and FX were eluted as separate fractions. The proteolytic activity, coming mainly from Factor VII Activating Protease (FSAP) (J. Roemisch, Biological Chemistry 383 (2002) 1119-1124) was also completely separated in this purification step. Further separation of the remaining contaminants from IαI/PαI containing fraction(s), namely traces of vitamin K dependant clotting factors FII, FVII and FX were achieved in the next step using hydroxylapatite chromatography.

All publications and patent documents cited in this application are incorporated by reference in their entirety for all purposes to the same extent as if each individual publication or patent document were so individually denoted. Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics,* 5th Ed., R. Rieger et al. (eds.), Springer Verlag (1991); and Hale & Marham, *The Harper Collins Dictionary of Biology* (1991).

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed is:

1. A process for producing a blood plasma-derived IαIp composition comprising a mixture of inter-alpha inhibitor protein (IαI) and pre-alpha protein (PαI), wherein the IαI and the PαI are present in said mixture in a physiological proportion, the process comprising:
   isolating from blood plasma a plasma fraction containing IαI and PαI, wherein the IαI and PαI are present in a physiological proportion; and
   purifying the plasma fraction to obtain an IαIp composition with a purity of IαIp ranging from about 85% to about 100% pure, wherein the purifying comprises hydroxylapatite chromatography.

2. The process of claim 1, wherein the isolating comprises solid phase extraction or chromatographing blood plasma.

3. The process of claim 1, wherein the plasma fraction comprises a side fraction obtained from the purification of clotting factor IX or from the purification of a prothrombin complex concentrate.

4. The process of claim 1, wherein the plasma fraction is isolated as a cryosupernatant resulting from cryoprecipitation of blood plasma.

5. The process of claim 1, wherein the plasma fraction is cryo-poor plasma.

6. The process of claim 1, wherein the plasma fraction is human, primate, bovine, porcine, feline, or canine.

7. The process of claim 1, further comprising obtaining blood, obtaining blood plasma, obtaining a side fraction obtained from the purification of clotting factor IX, obtaining a side fraction from the purification of a prothrombin complex concentrate, obtaining a cryosupernatant resulting from cryoprecipitation of blood plasma or obtaining cryo-poor plasma.

8. The process of claim 1, wherein the purifying further comprises affinity chromatography.

9. The process of claim 1, wherein the IαI and PαI present in the plasma fraction have an apparent molecular weight of between about 60,000 to about 280,000 kDa.

10. The process of claim 1, further comprising:
    purifying the plasma fraction; virus inactivating the plasma fraction and/or the purified IαIp; the addition of stabilizers; pasteurization of the purified IαIp;
    or anion-exchange chromatography of the purified IαIp.

11. The process of claim 10, wherein the further purifying the plasma fraction is by passing through heparin affinity column and collecting the flow through (unbound) fraction; the virus inactivating is by a solvent/detergent treatment or thermal inactivation; and the anion-exchange chromatography of the purified IαIp is diethylaminoethyl (DEAE) Sepharose.

12. The process of claim 11, wherein the thermal inactivation comprises pasteurization at a temperature of between about 55 to about 65° C. or dry heat at 70 to 120° C. omega-amino acids, sugar, or combinations thereof.

13. A composition of IαIp comprising a mixture of inter-alpha inhibitor protein (IαI) and pre-alpha protein (PαI), wherein the IαI and the PαI are present in said mixture in a physiological proportion and: have a high trypsin inhibitory specific activity between about 1000 to about 2000 IU/mg; have a half life of greater than one hour; comprise a light chain of inter-alpha inhibitor protein associated with at least one of three heavy chains H1, H2 and H3; or comprise a light chain of inter-alpha inhibitor protein associated with at least one of three heavy chains H1, H2, H3 and H4.

14. The composition of claim 13, wherein trypsin inhibitory specific activity is between about 1400 to about 2000 IU/mg.

15. The composition of claim 13, wherein the IαIp composition has a half life of at least 5 hours.

16. The composition of claim 13, wherein the IαIp composition has a half life of at least 10 hours.

17. A composition of IαIp comprising a mixture of inter-alpha inhibitor protein (IαI) and pre-alpha protein (PαI), wherein the IαI and the PαI are present in said mixture in a physiological proportion, said composition having been prepared by the process according to claim 1.

18. The composition of claim 17, further comprising an additional therapeutic agent.

19. The composition of claim 18, wherein the additional therapeutic agent is an anti-inflammatory agent, an anti-coagulant or an immunomodulator.

20. A pharmaceutical composition comprising a therapeutically effective amount of the composition of claim 17, and a pharmaceutically acceptable carrier.

21. A method of treating an inflammation related disorder comprising administering to a subject in need thereof a therapeutically effective amount of the composition of claim 17, wherein the inflammation related disorder is selected from an acute inflammatory disease, sepsis, septic shock, rheumatoid arthritis, meningitis, Crohn's Disease, chronic obstructed pulmonary disease and rhinitis.

22. The method of claim 21, wherein the IαIp is administered as a tablet, capsule, or injectables.

23. A method of treating an acute inflammatory disease, sepsis, septic shock, rheumatoid arthritis, meningitis, Crohn's Disease, chronic obstructed pulmonary disease and rhinitis in a subject, comprising:
(a) determining the pre-treatment level of one or more of the following levels in a subject:
(i) the level of IαI;
(ii) the level of PαI;
(iii) the level of IαIp;
(iv) the level of H3;
(v) the level of H4;
(vi) the level of H1;
(vii) the level of H2; and
(viii) the level of LC; and
(b) administering a therapeutically effective amount of the composition of claim 17 to the subject.

24. A method of monitoring the progress of a subject being treated with an IαIp therapy, comprising:
(a) determining the pre-treatment level of one or more of the following levels, in a subject:
(i) the level of IαI;
(ii) the level of PαI;
(iii) the level of IαIp;
(iv) the level of H3;
(v) the level of H4;
(vi) the level of H1;
(vii) the level of H2; and
(viii) the level of LC;
(b) administering a therapeutically effective amount of the composition of claim 17 to the subject; and
(c) determining the level of one or more of the levels in the subject after an initial period of treatment with the composition,
wherein an increase of the level in the subject following treatment with the composition indicates that the subject is likely to have a favorable clinical response to treatment with IαIp.

25. A kit comprising a composition according to claim 17 and instructions for therapeutic use.

* * * * *

UNITED STATES PATENT AND TRADEMARK OFFICE
CERTIFICATE OF CORRECTION

| | | |
|---|---|---|
| PATENT NO. | : 7,932,365 B2 | Page 1 of 1 |
| APPLICATION NO. | : 10/578449 | |
| DATED | : April 26, 2011 | |
| INVENTOR(S) | : Yow-Pin Lim et al. | |

It is certified that error appears in the above-identified patent and that said Letters Patent is hereby corrected as shown below:

At column 30, claim number 12, line number 62 should read:

12. The process of claim 11, wherein the thermal inactivation comprises pasteurization at a temperature of between about 55 to about 65°C. or dry heat at 70 to 120°C. ~~omega-amino acids, sugar, or combinations thereof.~~

Signed and Sealed this
Seventh Day of February, 2012

David J. Kappos
*Director of the United States Patent and Trademark Office*